United States Patent [19]

Trust et al.

[11] 4,168,385
[45] Sep. 18, 1979

[54] HYPOLIPEMIC PHENYLACETIC ACID DERIVATIVES

[75] Inventors: Ronald I. Trust, Highland Falls; Francis J. McEvoy, Pearl River; Jay D. Albright, Nanuet, all of N.Y.

[73] Assignee: American Cyanamid Company, Stamford, Conn.

[21] Appl. No.: 769,742

[22] Filed: Feb. 17, 1977

Related U.S. Application Data

[63] Continuation-in-part of Ser. No. 616,806, Sep. 25, 1975, abandoned.

[51] Int. Cl.$^2$ .............................................. C07C 69/76

[52] U.S. Cl. ........................................ 560/56; 560/10; 560/17; 560/59; 560/61; 560/62; 560/63; 562/427; 562/431; 562/466; 562/469; 562/471; 562/472; 424/304; 424/308; 424/317; 260/465 D

[58] Field of Search ............... 260/520 C, 516, 465 D; 560/62, 63, 17, 10, 56, 61, 59; 562/431, 471, 472, 427, 466, 469

[56] References Cited

U.S. PATENT DOCUMENTS

| | | | |
|---|---|---|---|
| 3,378,582 | 4/1968 | Bolhofer | 560/17 |
| 3,517,051 | 6/1970 | Bolhofer | 260/520 C |
| 3,740,437 | 6/1973 | Harrison et al. | 260/520 C |
| 4,067,996 | 1/1978 | Najer et al. | 560/62 |
| 4,072,754 | 2/1978 | Schacht et al. | 562/472 |

*Primary Examiner*—Jane S. Myers
*Attorney, Agent, or Firm*—Claude J. Caroli

[57] ABSTRACT

This invention discloses α-aryloxy or α-arylthio para substituted phenyl acetic acid compounds that are useful in lowering sterol and triglyceride serum levels.

12 Claims, No Drawings

HYPOLIPEMIC PHENYLACETIC ACID DERIVATIVES

CROSS REFERENCE TO RELATED APPLICATIONS

This application is a continuation-in-part of our co-pending application, Ser. No. 616,806 filed Sept. 25, 1975, now abandoned.

DESCRIPTION OF THE PRIOR ART

Netherlands Application No. 7,209,182-Q (1972) discloses (4-phenoxy-α-phenoxy)acetic acid derivatives of the formula:

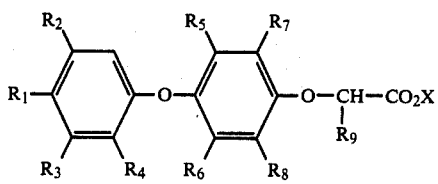

wherein $R_1$ is H, MeS, cyclopentyl, methyl-cyclohexyl, ethyl-cyclohexyl, cyclohexyl or phenyl and $R_9$ is alkyl ($C_1$-$C_{10}$) or phenyl. It is alleged that these compounds are useful as hypolipemics.

Other patents or applications disclosing various phenoxy-phenylacetic acid derivatives include: West German Pat. No. 1,518,011 (1969); Netherlands Pat. No. 6,503,523 (1965); Netherlands Pat. No. 7,301,246-C (1973); Gt. Britain Pat. No. 1,216,882-R (1967); Belgian Pat. No. 790,363-Q (1971) and Belgian Pat. No. 812,108 (1973).

BRIEF SUMMARY OF THE INVENTION

This invention discloses hypolipemic compounds that can be represented by the formula:

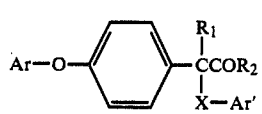

wherein

X is selected from the group consisting of oxygen and sulfur;

$R_1$ is selected from the group consisting of hydrogen and lower alkyl;

$R_2$ is selected from the group consisting of hydroxy, lower alkoxy, lower alkoxyethoxy, 2,3-dihydroxypropoxy and 3-loweralkoxy-2-hydroxypropoxy;

Ar is an aryl selected from the group consisting of phenyl, naphthyl, 4-chloro-1-naphthyl and substituted phenyl wherein the substituents are cyano, halogen, hydroxy, trihalomethyl, nitro, amino, lower alkyl, lower alkoxy, loweralkylsulfonyl, loweralkylamino, diloweralkylamino and loweralkanoylamino;

Ar' is an aryl selected from the group consisting of phenyl, naphthyl, 5,6,7,8-tetrahydro-1-naphthyl, 5,6,7,8-tetrahydro-2-naphthyl, 4-chloro-5,6,7,8-tetrahydro-1-naphthyl, 4-chloro-1-naphthyl, 4-indanyl, 5-indanyl, 1,1-diloweralkyl-6-indanyl, 1,1-diloweralkyl-5-indanyl, 5,5-diloweralkyl-5,6,7,8-tetrahydro-2-naphthyl, 8,8-diloweralkyl-5,6,7,8-tetrahydro-2-naphthyl, 7-halo-4-indanyl, substituted phenyl wherein the phenyl substituents are halogen, trihalomethyl, lower alkyl, lower alkoxy, cyano, phenyl, phenoxy, halophenoxy, benzyloxy and cycloalkyl; and where $R_2$ is OH, the alkali metal or organic base carboxylic salts thereof.

A more preferred embodiment of the present invention is encompassed by compounds of the formula:

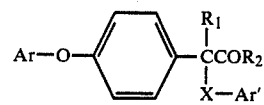

wherein

X is selected from the group consisting of oxygen and sulfur;

$R_1$ is selected from the group consisting of hydrogen and lower alkyl;

$R_2$ is selected from the group consisting of hydroxy, lower alkoxy, lower alkoxyethoxy, 2,3-dihydroxypropoxy and 3-lower alkoxy-2-hydroxypropoxy;

Ar is an aryl selected from the group consisting of phenyl, naphthyl, 4-chloro-1-naphthyl and substituted phenyl wherein the substituents are cyano, halogen, trihalomethyl, lower alkyl and lower alkanoylamino;

Ar' is an aryl selected from the group consisting of phenyl, naphthyl, 5,6,7,8-tetrahydro-1-naphthyl, 5,6,7,8-tetrahydro-2-naphthyl, 4-chloro-5,6,7,8-tetrahydro-1-naphthyl, 4-chloro-1-naphthyl, 4-indanyl, 5-indanyl, 7-halo-4-indanyl and substituted phenyl wherein the phenyl substituents are halogen, trihalomethyl, lower alkyl, cyclohexyl, cyclopentyl, adamantyl, lower alkoxy, phenyl, phenoxy halophenoxy and benzyloxy; and Where $R_2$ is OH, the alkali metal or organic base carboxylic salts thereof.

A most preferred embodiment of the present invention is encompassed by compounds of the formula:

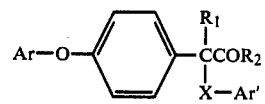

wherein

X is selected from the group consisting of oxygen and sulfur;

$R_1$ is selected from the group consisting of hydrogen and lower alkyl;

$R_2$ is selected from the group consisting of hydroxy, lower alkoxy, lower alkoxyethoxy, 2,3-dihydroxypropoxy and 3-loweralkoxy-2-hydroxypropoxy;

Ar is an aryl selected from the group consisting of phenyl, naphthyl, 4-chloro-1-naphthyl and mono or di-substituted phenyl wherein the substituents are cyano, chloro, fluoro, trihalomethyl, lower alkyl and lower alkanoylamino;

Ar' is an aryl selected from the group consisting of phenyl, naphthyl, 5,6,7,8-tetrahydro-1-naphthyl, 5,6,7,8-tetrahydro-2-naphthyl, 4-chloro-5,6,7,8-tetrahydro-1-naphthyl, 4-chloro-1-naphthyl, 4-indanyl, 5-indanyl, 7-halo-4-indanyl and mono or di-substituted phenyl wherein the phenyl substituents are chloro, fluoro, trihalomethyl, lower alkyl, cyclohexyl, cyclopentyl, adamantyl, lower alkoxy, phenyl, phenoxy, chlorophenoxy, fluorophenoxy and benzyloxy;

and where $R_2$ is OH, the alkali metal or organic base carboxylic salts thereof.

Suitable carboxylic acid salts of the compounds wherein $R_2$ is OH are the sodium and potassium salts as well as amine salts with organic bases such as ammonia, methylamine, dimethylamine, triethylamine, trimethylamine, pyridine, 2-hydroxyethylamine, tris(2-hydroxyethyl)amine, piperidine and the like.

Suitable lower alkoxy groups contemplated by the invention are those having 1–6 carbon atoms such as methoxy, ethoxy, isopropoxy, propoxy, tert-amyloxy, tert-butoxy and n-hexyloxy. Suitable lower alkyl groups contemplated by the invention are those having 1–6 carbon atoms such as methyl, ethyl, isopropyl, propyl, tert-amyl, tert-butyl, n-hexyl and the like.

The invention is also concerned with a method of lowering sterol and triglyceride serum levels in mammals by orally administering the above compounds in therapeutic compositions.

DETAILED DESCRIPTION OF THE INVENTION

The novel compounds of the present invention are in general colorless or yellow crystalline solids or colorless, pale yellow or tan oils. The compounds are in general soluble in organic solvents such as chloroform, dichloromethane, dimethylsulfoxide and lower alkanols.

In general the novel compounds of the invention are prepared by reacting a p-aryloxy-phenylacetic acid or ester of formula A ($R_2$=OH or loweralkoxy) with a halogenating agent to give an intermediate α-halo p-substituted aryloxy-, phenylacetic acid or ester of formula B.

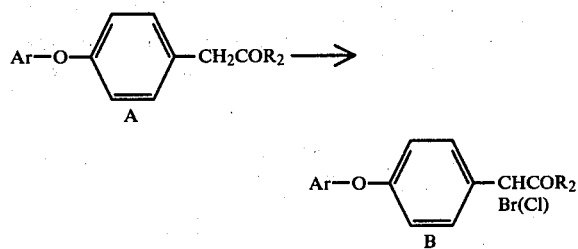

α-Halogenation of intermediates A may be carried out with reagents such as N-bromosuccinimide (NBS), N-chlorosuccinimide (NCS), bromine, chlorine, sulfuryl-chloride and the like. The α-halogenations with NBS and NCS are best carried out on the acids ($R_2$=OH) or on the esters ($R_2$=loweralkoxy) by heating in inert solvents such as dichloromethane, carbon tetrachloride and the like. The reaction may be catalyzed by the addition of hydrogen bromide to the NBS reactions and hydrogen chloride to the NCS reactions. The reactions are in general complete in 3–24 hours; however, some reactions may require longer reaction times. The α-halogenation reactions may be catalyzed with heavy metals as for example thallium salts.

The α-halo intermediates B may be prepared by reacting the acids of formula A ($R_2$=OH) with thionyl chloride or other acid chloride forming reagents to give the corresponding acid chlorides and then halogenating with NBS, NCS, bromine, chlorine or sulfuryl chloride to give α-halo-p-aryloxy, phenylacetyl chlorides. Reaction with lower alkanols then gives the intermediates of formula B ($R_2$=loweralkoxy) while reaction with water gives the intermediates of formula B wherein $R_2$=OH.

The intermediates of formula B ($R_2$=OH or loweralkoxy) are reacted with phenolic compounds such as phenol, substituted phenols, thiophenols and substituted thiophenols to give the novel compounds of formula I ($R_2$=OH, or lower alkoxy) of the invention.

The reaction of appropriately substituted α-halophenylacetic acids and α-halophenylacetates with phenolic compounds may be carried out in inert solvents such as lower alkanols, dimethyl sulfoxide, N,N-dimethylformamide, N,N-dimethylacetamide, xylene, toluene, tetrahydrofuran, acetone, hexamethylphosphoramide and the like in the presence of a base to first convert the phenolic compound or thiophenol to the corresponding phenoxide or thiophenoxide. Bases such as loweralkoxides, sodium hydride, potassium hydride, sodium carbonate or potassium carbonate and the like may be used to prepare the phenoxides and thiophenoxides which are reacted with compounds of formula B (wherein $R_2$=OH or loweralkoxy) to give displacement of the α-halogen atom and introduction of the desired α-aryloxy- and α-arylthio- substituents. The displacement reaction is conveniently carried out in refluxing methanol or methanol-benzene with sodium methoxide as base for 2–24 hours or in refluxing acetone with potassium carbonate for 10–30 hours.

The desired intermediate p-substituted phenylacetic esters of formula A ($R_2$=loweralkoxy) may also be prepared from p-aryloxy-, acetophenones by reaction with thallium nitrate. The reaction with thallium nitrate is generally carried out in methanol to give the methyl esters (formula A, $R_2$=OCH$_3$) which may be halogenated to give α-halo derivatives of formula B wherein $R_2$=OCH$_3$.

Alternatively, the p-aryloxy-, acetophenones may be heated with sulfur and morpholine (Wilgerodt reaction) and the intermediate thiomorpholides hydrolyzed to give the substituted phenylacetic acids of formula A wherein $R_2$=OH, or heated in an alcoholic solvent with mineral acid to give the substituted esters of formula A wherein $R_2$=loweralkoxy. Coupling of phenols with p-halo phenylacetic acid and esters with copper catalysts also give the desired intermediates of formula A wherein $R_2$=OH or loweralkoxy.

[p-(p-Cyanophenoxy)phenyl]acetic acid and [p-(p-nitrophenoxy)phenyl]acetic acid are prepared by reaction of p-hydroxyphenylacetic acid with either p-bromo or p-fluorobenzonitrile or 1-chloro-4-nitrobenzene or 1-fluoro-4-nitrobenzene, respectively. The [p-(p-nitrophenoxy)phenyl]acetic acid may be reduced to give [p-(p-aminophenoxy)phenyl]acetic acid which may be diazotized and the diazonium salt used to prepare [p-(p-hydroxyphenoxy)phenyl]acetic acid, [p-(p-cyanophenoxy)phenyl]acetic acid or [p-(p-halophenoxy)-phenyl]acetic acid. These derivatives are useful intermediates for the preparation of some of the novel compounds of formula I of this invention.

The esters of formula I wherein $R_2$ is as previously defined are prepared by the reaction of acid chlorides of formula C with the appropriate hydroxy compounds. Alternatively, the lower alkyl esters

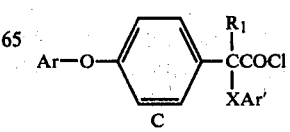

-continued

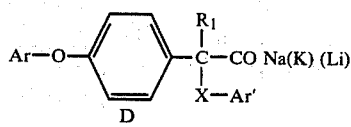

of formula I ($R_2$=methoxy or ethoxy) may be reacted with a hydroxy compound in an ester exchange reaction to give the desired esters of formula I. Lower alkyl halides and appropriately substituted lower alkyl halides may be reacted with the carboxylic salts of formula D to give the desired esters of formula I. For example, carboxylic acid salts of formula D may be reacted with 3-halo-1,2-propanediol to give the 2,3-hydroxypropyl esters of formula I. The reactions of the alkali metal salts of formula D with loweralkyl halides and appropriately substituted loweralkyl halides are best carried out in a solvent such as hexamethylphosphoramide at 50°–150° C. for 1–10 hours.

The novel compounds of this invention of formula I wherein $R_1$ is lower alkyl may be prepared from the acid ($R_2$=OH) or ester ($R_2$=lower alkoxy) derivatives of formula I by first preparation of the dianions of the acids ($R_2$=OH) or of the mono carbanions of the esters ($R_2$=loweralkoxy) with suitable strong bases (for example lithium diisopropylamide or sodamide). Reaction of these dianions or carbanions with either lower alkyl halides gives the compounds of formula I where $R_1$ is loweralkyl. The reactions may be carried out at 0° to −78° C. in inert solvents such as tetrahydrofuran, tetrahydrofuran-hexamethylphosphoramide and the like.

The compounds of the present invention show hypolipidemic activity. The mechanism of action of these compounds is not known and the inventors do not wish to be limited to any particular mechanism. However, the compounds of the present invention were shown to possess hypolipidemic activity as determined by animal experiments as follows: The compounds were administered orally admixed with the diet to groups of 2–6 male rats, Cobs CD from Charles River. A control group of 6–8 rats was maintained on the diet alone: test groups were maintained on the diet plus the indicated percentage of compound by weight. After 5 days treatment serum sterol concentrations were determined either (1) according to the saponification and extraction method of P. Trinder, Analyst 77, 321 (1952) and the colorimetric determination of Zlatkis, et al, J. Lab. Clin. Med. 44, 486 (1953) or (2) by the extraction method of H. H. Leffler, Amer. J. Clin. Path. 31, 310 (1959), the overall method appropriately modified for use with an automatic mechanical analyzer. Serum triglycerides were estimated by the automated procedure of Kessler and Lederer ["Automation in Analytical Chemistry", Skeggs, L. T., Ed., Mediad Inc., New York, 1965, p. 341]. In these tests a compound is considered to have hypolipidemic activity if it depresses serum sterol levels 15% or more below that of the controls, and/or depresses triglyceride levels by 25% or more below controls. Table I shows several of the compounds of the present invention and the degree to which they depress serum sterols and triglyceride levels after a 5 day dosing period.

Table I

| Compound | Dose | % Lowering of Sterols | % Lowering of Triglycerides |
| --- | --- | --- | --- |
| Methyl α(p-chlorophenoxy)-α-[p-(p-chlorophenoxy)phenyl]acetate | 0.1% | 44 | 60 |
| Methyl α(phenoxy)-α-[p-(p-chlorophenoxy)phenyl]acetate | 0.1% | 23 | 54 |
| Methyl α(p-chlorophenylthio)-α-[p-(p-chlorophenoxy)phenyl]acetate | 0.1% | 34 | 57 |
| Methyl α(phenylthio)-α-[p-(p-chlorophenoxy)phenyl]acetate | 0.1% | 38 | 35 |
| α(Phenoxy)-α-[p-(p-chlorophenoxy)phenyl]acetic acid | 0.1% | 30 | 55 |
| Methyl α(p-chlorophenoxy)-α-[p-(phenoxy)phenyl]acetate | 0.1% | 12 | 58 |
| Methyl α(phenoxy)-α-[p-(phenoxy)phenyl]acetate | 0.1% | 21 | 58 |
| Methyl α(p-chlorophenylthio)-α-[p-(phenoxy)phenyl]acetate | 0.1% | 20 | 47 |
| α(Phenylthio)-α-[p-chlorophenoxy)phenyl]acetic acid | 0.1% | 32 | 44 |
| α(Phenoxy)-α-[p-(phenoxy)phenyl]acetic acid | 0.1% | 22 | 51 |
| α(p-Chlorophenylthio)-α-[p-(phenoxy)phenyl]acetic acid | 0.1% | 20 | 39 |
| α(p-Fluorophenoxy)-α-[p-(p-chlorophenoxy)phenyl]acetic acid | 0.1% | 29 | 58 |
| Methyl α[p-(benzyloxy)phenyl]-α-[p-(p-chlorophenoxy)phenyl]acetate | 0.1% | 29 | 57 |
| α[p-(p-Phenoxy)phenoxy]-α-[p-(p-chlorophenoxy)phenyl]acetic acid | 0.1% | 33 | 54 |
| Methyl α(phenoxy)-α-[p-(p-chlorophenylthio)phenyl]acetate | 0.03% | 6 | 52 |
| Methyl α(p-tert-butylphenoxy)-α-[p-(p-chlorophenoxy)phenyl]acetate | 0.1% | 20 | 56 |
| Methyl α(m-tert-butylphenoxy)-α-[p-(p-chlorophenoxy)phenyl]acetate | 0.1% | 41 | 63 |
| Methyl α(α,α,α-trifluoro-m-tolyloxy)-α-[p-(p-chlorophenoxy)phenyl]acetate | 0.1% | 29 | 61 |
| Methyl α(3-biphenylyloxy)-α-[p-(p-chlorophenoxy)phenyl]acetate | 0.1% | 29 | 66 |
| Methyl α(4-chloro-1-naphthyloxy)-α-[p-(p-chlorophenoxy)phenyl]acetate | 0.1% | 11 | 32 |
| Methyl α(p-cyclohexylphenoxy)-α-[p-(p-chlorophenoxy)phenyl]acetate | 0.1% | 51 | 64 |
| Methyl α(3,4,5-trichlorophenoxy)-α-[p-(p-chlorophenoxy)phenyl]acetate | 0.1% | 30 | 55 |

The novel compounds of the present invention have been found to be highly useful as hypolipemic agents in mammals when administered orally in amounts ranging from about 0.2 mg. to about 25 mg. per kg. of body weight per day. A preferred dosage regimen for optimum results would be from about 0.5 mg. to about 6 mg. per kg. of body weight per day, and such dosage units are employed that a total of from about 35 mg. to about 420 mg. of the mixture for a subject of about 70 kg. body weight are administered in a 24 hour period.

The hypolipemic compounds of the present invention may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the mixtures may be incorporated with excipients and used in the form of tablets, troches, capsules, elixirs, suspensions, syrups, wafers, and the like. Such compositions and preparations should contain at least 0.1% of hypolipemic agent. The percentage of active ingredient in the compositions and preparations may, of course, be varied and may conveniently be between about 5% to about 25% of the weight of the unit. The amount of mixture in such therapeutically useful compositions is such that a suitable dosage will be obtained. Preferred compositions or preparations according to the present invention are prepared so that an oral dosage unit form contains between about one and 200 milligrams of hypolipemic agent.

The tablets, troches, pills, capsules and the like may also contain the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier such as a fatty oil. Various other materials may be present as coatings or to otherwise modify the physical form of the dosage unit. For instance, tablets, pills or capsules may be coated with shellac, sugar or both. A syrup or elixir may contain the active mixtures, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed.

This invention will be described in greater detail in conjunction with the following specific examples. The following examples are given for the purpose of illustration and are not intended to limit the scope of the invention.

EXAMPLE 1

[p-(p-Nitrophenoxy)phenyl]acetic Acid

A mixture of 38 g of p-hydroxyphenylacetic acid, 39.4 g of 4-nitrochlorobenzene and 69 g of anhydrous potassium carbonate in 275 ml of N,N-dimethylacetamide is heated to 155°–160° C. over 2 hours, and maintained at that temperature, under Argon atmosphere for 4 hours with vigorous stirring. On cooling, an orange solid separated. A 1000 g solution of 5% NaHCO$_3$ is added, resulting in a red brown solution. The solution is extracted with 4×100 ml of ether. The aqueous layer is acidified by the dropwise addition of 150 ml of concentrated HCl. A light yellow solid precipitates and is filtered and washed with 1500 ml of H$_2$O to give the product, mp 132°–136° C. A sample is recrystallized from 19:1 methanol-water, to give the product, mp 135°–137° C.

EXAMPLE 2

[p-(p-Aminophenoxy)phenyl]acetic Acid

To a solution of 13.65 g of [p-(p-nitrophenoxy)phenyl]acetic acid in 100 ml of ethanol is added 130 mg of platinum oxide. The mixture is shaken under 45 lb of hydrogen pressure in a Parr shaker. After 2 hours, a thick white solid precipitates. The mixture is filtered, and 200 mg of fresh platinum oxide is added to the filtrate which is subjected to the reducing conditions. After an additional hour, the mixture is filtered and washed with cold ethanol. The combined solids are dissolved in hot methanol and filtered. Water is added to the filtrate to afford 4.9 g of a brown solid. A portion is recrystallized from methanol to yield the product as cream colored crystals, mp 172° C. (dec.).

EXAMPLE 3

[p-(p-Cyanophenoxy)phenyl]acetic Acid

To a solution of 15.2 g of p-hydroxyphenylacetic acid and 12.1 g of p-fluorobenzonitrile in 125 ml of N,N-dimethylacetamide is added, with vigorous stirring, 27.6 g of anhydrous potassium carbonate. The mixture is heated at 155°–160° C. under an Argon atmosphere with rapid stirring for 4 hours. After cooling to room temperature the mixture is poured into 300 ml of saturated NaHCO$_3$. The mixture is extracted with two 100 ml portions of ether. The aqueous layer is acidified with 50 ml of concentrated HCl. The product is filtered washed with water (ca 500 ml) and dried to give a white solid mp 125.5°–127.5° C. A portion is recrystallized from 7:3 methanol-water (10 ml) to give white needles, mp 126.5°–128.5° C.

EXAMPLE 4

Ethyl [p-(p-nitrophenoxy)phenyl]acetate

A solution of 27.3 g of [p-(p-nitrophenoxy)phenyl]acetic acid in 270 ml of ethanol is cooled to 0° C. and saturated with dry HCl gas over 3½ hours. The resulting deep red solution is heated to reflux and maintained at reflux overnight. A yellow crystalline solid separates on cooling. The entire mixture is poured into 500 ml of water and extracted with three 200 ml portions of benzene. The combined extracts are washed with two 150 ml portions of water, two 150 ml portions of saturated NaHCO$_3$, 150 ml of saturated brine, and dried over MgSO$_4$. Evaporation of the solvent at reduced pressure affords an oil which yields yellow crystals from 50 ml of ethanol, mp 70.5°–73° C. Recrystallization from ethanol affords yellow prisms, mp 70.5°–73° C.

EXAMPLE 5

[p-(p-Chlorophenylthio)phenyl]acetic Acid

A solution of 6.0 g of 4-chlorothiophenol and 8.0 g of potassium hydroxide in 80 ml of water is heated to 50° C. and 0.8 g of copper powder and 10.4 g of 4-iodophenylacetic acid are added. The mixture is heated to reflux and maintained at reflux overnight. The mixture is then cooled and filtered. The filtrate is acidified with concentrated HCl to give a white solid which, on recrystallization from methanol, yields cream colored plates, mp 135°–140° C. A sample is recrystallized from chloroform-hexane to give white plates, mp 144.5°–148° C.

EXAMPLE 6

Ethyl[p-(p-aminophenoxy)phenyl]acetate

A mixture of 7.5 g of ethyl[p-(p-nitrophenoxy)phenyl]acetate and 200 mg of platinum oxide in 200 ml of ethanol is shaken under 45 lbs of hydrogen for one hour and then filtered through diatomaceous earth which is washed with 20 ml of ethanol. The combined filtrate and washings are concentrated to a yellow oil. Bulb-to-bulb distillation affords a pale yellow opaque oil, b.p. 176° @ 0.1 mm.

EXAMPLE 7

Ethyl[p-(p-N-octylaminophenoxy)phenyl]acetate

A slurry of 3.45 g of anhydrous potassium carbonate in 50 ml of hexamethylphosphoramide (HMPA) containing 6.8 g of ethyl[p-(p-aminophenoxy)phenyl]acetate is heated to 50° C. A solution of 6 g of n-octyliodide in 10 ml of HMPA is added over 2 hours. The heating is continued for 24 hours. The mixture is diluted with 100 ml of $H_2O$ and extracted with two 100 ml portions of ether. The combined extracts are washed with two 100 ml portions of $H_2O$, 100 ml of saturated brine, and dried over $MgSO_4$. Evaporation of the solvent at reduced pressure affords a brown liquid, which yields, after silica gel chromatography (benzene, then $CHCl_3$) and bulb-to-bulb distillation of the $CHCl_3$ eluate, a pale yellow oil, b.p. 194° @ 0.05 mm.

EXAMPLE 8

Ethyl[p-(p-N,N-dioctylaminophenoxy)phenyl]acetate

Bulb-to-bulb distillation (210° @ 0.05 mm) of the benzene eluate from Example 7 affords the product as a pale yellow oil.

EXAMPLE 9

Ethyl[p-(p-acetylaminophenoxy)phenyl]acetate

To a mixture of 6.8 g of ethyl[p-(p-aminophenoxy)phenyl]acetate, 7.5 ml of acetic acid, 5.4 ml of water and 8.75 g of crushed ice, maintained at 0°-5° C. is added 2.8 g of acetic anhydride. The temperature immediately rises to 15° C. The stirring is continued for two hours, and extracted with two 50 ml portions of ether. The combined extracts are washed with 50 ml of $H_2O$, 50 ml of saturated $NaHCO_3$, 50 ml of saturated brine, and dried over $MgSO_4$. Evaporation of the solvent affords the product as a tan solid, mp 95°-102° C. A portion is recrystallized from ethanol-hexane to give the product, mp 105°-107° C.

EXAMPLE 10

Methyl[p-(p-chlorophenylthio)phenyl]acetate

A mixture of 21 g of [p-(p-chlorophenylthio)phenyl]acetic acid and 11.9 g of thionyl chloride are stirred overnight at room temperature. To the resulting greenish yellow solution is added 20 ml of benzene and the solvent is evaporated at reduced pressure. This procedure is repeated once. The residue is added dropwise to 300 ml of methanol, maintained at 0° C., and the resulting solution is stirred overnight. The solvent is evaporated at reduced pressure and the mixture is dissolved in 200 ml of ether. The ether layer is washed with 100 ml of water, 100 ml of saturated $NaHCO_3$, 100 ml of saturated brine and dried over $MgSO_4$. Evaporation of the solvent and distillation of the residue affords the product as a light yellow oil.

EXAMPLE 11

[p-(p-Chlorophenylsulfinyl)phenyl]acetic Acid

To a solution of 4.49 g of sodium metaperiodate in 80 ml of water is added a solution of 5.57 g of [p-(p-chlorophenylthio)phenyl]acetic acid in 75 ml of 1.75% NaOH. A white solid precipitates immediately. After stirring overnight the mixture is filtered and the filtrate is acidified with concentrated HCl to give a white solid. This product, which contains some starting material, is reworked, as above, to yield the pure product. Recrystallization from chloroform-hexane affords white crystals, mp 139°-141° C. and 144°-148.5° C.

EXAMPLE 12

[p-(p-Chlorophenylsulfonyl)phenyl]acetic Acid

To a solution of 5.57 g of [p-(p-chlorophenylthio)phenyl]acetic acid in glacial acetic acid is added 25 ml of 30% hydrogen peroxide. The mixture is heated to 70° C. forming a clear yellow solution. The mixture is maintained at 70° C. for 3 hours and then cooled to give a white precipitate on washing with water, mp 153°-157° C. Recrystallization from chloroform affords the product as fine white needles, mp 156.5°-159° C.

EXAMPLE 13

Methyl α-Bromo-α-[p-(p-chlorophenoxy)phenyl]acetate

To a solution of 1.38 g of methyl α-[p-(p-chlorophenoxy)phenyl]acetate in 15 ml of carbon tetrachloride is added 0.92 g of N-bromosuccinimide and a small drop of concentrated HBr. The mixture is maintained at reflux for 72 hours and cooled to room temperature. Filtration through 50 g of aluminum oxide, evaporation of the solvent and bulb-to-bulb distillation of the residue (166° @ 0.05 mm) affords the product as a colorless oil.

EXAMPLE 14

Methyl Bromo[p-(phenoxy)phenyl]acetate

A mixture of 22.68 g of methyl[p-(phenoxy)phenyl]acetate, 17.195 g of N-bromosuccinimide and 20 drops of carbon tetrachloride saturated with HBr in 300 ml of carbon tetrachloride is heated at reflux for 28 hours. After cooling, the mixture is filtered through aluminum oxide, concentrated and distilled at 0.15 mm to give the product as a colorless oil (bp 162.5°-165° C.).

EXAMPLE 15

Methyl [p-(phenylthio)phenyl]acetate

A solution of 6.9 g of methyl 4-iodophenylacetate and 4.74 g of cuprous phenylmercaptide in 250 ml of pyridine is heated to reflux and maintained at reflux under Argon for 18 hours. The resulting brown solution is poured into 500 ml of water and extracted with 200 ml of ether. The organic extract is washed with 200 ml each of 10% HCl, saturated $NaHCO_3$, saturated brine and dried over $MgSO_4$. Evaporation of the solvent at reduced pressure affords a brown liquid, which is filtered through aluminum oxide (benzene eluant). The benzene is evaporated and the residue is distilled (128° C. @ 0.05 mm) to yield the product as a colorless liquid.

EXAMPLE 16

Methyl α-(p-chlorophenoxy)-α-[p-(p-chlorophenoxy)phenyl]acetate

To a solution of 1.19 g of sodium methoxide in 40 ml of methanol is added 3.21 g of 4-chlorophenol. A few crystals of potassium iodide are added, followed by a solution of 7.11 g of methyl α-bromo-α-[p-(p-chlorophenoxy)phenyl]acetate in 10 ml of benzene. The solution is heated at reflux overnight. After cooling to room temperature, the solution is poured into 100 ml of water and extracted with two 100 ml portions of ether. The combined extracts are washed with 50 ml of 5% NaOH, 50 ml of saturated brine and dried over $MgSO_4$. The solvent is evaporated at reduced pressure and the residue is triturated with petroleum ether to give the product as white crystals, mp 100°–101.5° C.

EXAMPLE 17

Methyl α-(phenoxy)-α-[p-(p-chlorophenoxy)phenyl]acetate

By a procedure identical with Example 16, except for the use of phenol as reactant, there is isolated the product as a colorless oil.

EXAMPLE 18

Methyl α-(p-chlorophenylthio)-α-[p-(p-chlorophenoxy)phenyl]acetate

Methyl α-bromo-α-[p-(p-chlorophenoxy)phenyl]acetate (7.11 g) is reacted with 3.61 g of 4-chlorothiophenol in methanol, as in Example 16, to give a yellow oil which is bulb distilled at 0.01 mm to afford a colorless oil (188° C.) which solidifies to give white crystals, mp 71°–75° C. A portion is recrystallized from hexane to give white needles, mp 74°–75.5° C.

EXAMPLE 19

Methyl α-(phenylthio)-α-[p-(p-chlorophenoxy)phenyl]acetate

Methyl α-bromo-α-[p-(p-chlorophenoxy)phenyl]acetate (7.11 g) is reacted with 2.75 g of thiophenol in methanol, as in Example 16, to yield a yellow oil. After a brief distillation at 0.02 mm to remove volatile impurities, the residue is evaporatively distilled (173° C. @ 0.01 mm) to afford the product as a colorless oil which solidifies, mp 64°–68.5° C. A portion is recrystallized from hexane to give white plates, mp 71.5°–72.5° C.

EXAMPLE 20

α-(Phenoxy)-α-[p-(p-chlorophenoxy)phenyl]acetic Acid

A mixture of 4.4 g of methyl α-(phenoxy)-α-[p-(p-chlorophenoxy)phenyl]acetate, 27 g of 20% KOH, and 20 ml of methanol is refluxed overnight. After cooling to room temperature, the methanol is removed at reduced pressure. The residue is dissolved in 100 ml of H$_2$O and extracted with 100 ml of ether. The aqueous layer is acidified with concentrated HCl and a yellow oil separates. The mixture is extracted with two 50 ml portions of chloroform. The combined extracts are washed with 50 ml of water and saturated brine and dried over MgSO$_4$. Evaporation of the solvent at reduced pressure affords the product as a white solid, mp 114°–115.5° C., after trituration with petroleum ether.

EXAMPLE 21

Methyl α-(p-chlorophenoxy)-α-[p-(phenoxy)phenyl]acetate

Methyl α-bromo-α-[p-(phenoxy)phenyl]acetate (6.42 g) is reacted with 3.21 g of 4-chlorophenol in methanol as in Example 16 to afford a white solid, which is recrystallized from hexane to yield the product, mp 99°–102° C.

EXAMPLE 22

Methyl α-(phenoxy)-α-[p-(phenoxy)phenyl]acetate

Methyl α-bromo-α-[p-(phenoxy)phenyl]acetate (6.42 g) is reacted with 2.35 g of phenol in methanol as in Example 16 to afford 6 g of a yellow liquid after distillation (154° C. at 0.15 mm). A 2.2 g portion is purified by chromatography on silica gel (60 g) with benzene eluent to give the product as a white solid, mp 75.5°–77° C. (from pet. ether).

EXAMPLE 23

Methyl α-(p-chlorophenylthio)-α-[p-(phenoxy)phenyl]acetate

Methyl α-bromo-α-[p-(phenoxy)phenyl]acetate (6.42 g) is reacted with 3.61 g of 4-chlorothiophenol in methanol as in Example 16 to afford a yellow oil which solidifies on standing. Recrystallization from 50 ml of petroleum ether affords the product as white crystals, mp 66°–67.5° C.

EXAMPLE 24

α-(Phenylthio)-α-[p-(p-chlorophenoxy)phenyl]acetic Acid

A mixture of 4.22 g of methyl α-(phenylthio)-α-[p-chlorophenoxy)phenyl]acetate, 20 ml of 20% KOH and 5 ml of methanol is refluxed overnight. The resulting two phase mixture is diluted with 500 ml of water and acidified with concentrated HCl to afford a semisolid product. The mixture is extracted with two 100 ml portions of chloroform. The combined extracts are washed with 100 ml of water, saturated brine, and dried over MgSO$_4$. A white crystalline solid is obtained on evaporation of the solvent. Recrystallization from chloroform affords white crystals, mp 156°–157.5° C.

EXAMPLE 25

α-(Phenoxy)-α-[p-(phenoxy)phenyl]acetic Acid

A mixture of 3.75 g of methyl α-(phenoxy)-α-[p-(phenoxy)phenyl]acetate in 20 ml of 20% KOH and 5 ml of methanol is refluxed overnight to afford, after acidification, a white solid, mp 144°–146° C. (from chloroform-petroleum ether).

EXAMPLE 26

[p-(p-Methylsulfonylphenoxy)phenyl]acetic Acid

A mixture of 30.4 g of p-hydroxyphenylacetic acid, 38.12 g of p-chlorophenyl methylsulfone, 55.2 g of potassium carbonate and 250 ml of N,N-dimethylacetamide is heated under Argon overnight at 150°–155° C. with vigorous stirring. The mixture is cooled, diluted with 500 ml of H$_2$O, and extracted with two 200 ml portions of benzene. Acidification of the aqueous layer affords an amber oil which solidifies to a white solid, mp 122.5°–125° C. Recrystallization from chloroform affords the product as white needles, mp 127.5°–129.5° C.

EXAMPLE 27

α-(p-Chlorophenylthio)-α-[p-(phenoxy)phenyl]acetic Acid

A mixture of 3.55 g of methyl α-(p-chlorophenylthio)-α-[p-(phenoxy)phenyl]acetate, 20 ml of 20% KOH and 5 ml of methanol is refluxed overnight. The mixture is acidified and worked up to afford a light green solid which is crystallized from chloroform to yield the product as white crystals, mp 121°–125° C.

EXAMPLE 28

4'-(α,α,α-Trifluoro-m-tolyloxy)acetophenone

A mixture of 32.4 g of α,α,α-trifluoro-m-cresol, 27.62 g of p-fluoroacetophenone, 55.2 g of potassium carbonate and 250 ml of N,N-dimethylacetamide is heated under Argon overnight with vigorous stirring at 150°–155° C. After cooling the mixture is added to 500 ml of water and extracted with benzene. The combined extracts are washed with two 100 ml portions of 5% NaOH, 100 ml of H₂O, 100 ml of saturated brine, and dried over MgSO₄. Evaporation of the solvent at reduced pressure affords a brown liquid which is distilled to give the product as a pale yellow oil (bp 122°–142° C. @ 0.2 mm).

EXAMPLE 29

Methyl α-(p-chlorophenoxy)-α-(p-iodophenyl)acetate

To a mixture of 2.38 g of sodium methylate in 80 ml of methanol is added 6.42 g of 4-chlorophenol and a few crystals of potassium iodide. After ½ hour of stirring a solution of 14.2 g of methyl α-bromo-α-(p-iodophenyl)acetate in 6 ml of benzene is added. The mixture is refluxed overnight. After cooling to room temperature, the mixture is added to 200 ml of water and extracted with two 50 ml portions of chloroform. The combined organic layers are washed with 50 ml of 5% NaOH, 50 ml of H₂O, 50 ml of saturated brine, and dried over MgSO₄. Evaporation of the solvent affords the product as a white solid, mp 122°–125° C. A portion is recrystallized from petroleum ether to yield white crystals, mp 126°–127° C.

EXAMPLE 30

Methyl α-(phenoxy)-α-(p-iodophenyl)acetate

In a similar manner as in Example 29, 14.2 g of methyl α-bromo-α-(p-iodophenyl)acetate is reacted with 4.70 g of phenol in methanol to yield a white to light pink solid, mp 68°–71° C. Recrystallization from petroleum ether yields the product as white crystals, mp 72.5°–74° C.

EXAMPLE 31

Methyl α-(p-chlorophenylthio)-α-(p-iodophenyl)acetate

In a similar manner as in Example 29, 12.7 g of methyl α-bromo-α-(p-iodophenyl)acetate is reacted with 6.47 g of 4-chlorothiophenol in methanol to yield a white solid, mp 44°–46° C.

EXAMPLE 32

Methyl (phenylthio)(p-iodophenyl)acetate

In a similar manner as in Example 29, 14.2 g of methyl α-bromo-α-(p-iodophenyl)acetate is reacted with 5.5 g of thiophenol in methanol to yield white crystals, mp 62.5°–65° C.

EXAMPLE 33

Methyl α-(p-chlorophenoxy)[p-(phenylthio)phenyl]acetate

A mixture of 6.04 g of methyl α-(p-chlorophenoxy)(p-iodophenyl)acetate, 3.36 g of cuprous phenylmercaptide, and 800 mg of thiophenol in 150 ml of pyridine is heated under Argon overnight. The mixture is poured into 300 ml of water and extracted with two 100 ml portions of chloroform. The combined organic layers are washed with two 50 ml portions of 5% NaOH, two 50 ml portions of water, 50 ml of saturated brine and dried over MgSO₄. Evaporation of the solvent at reduced pressure yields an oil. After column chromatography (benzene) and bulb-to-bulb distillation (173° C. @ 0.01 mm) there is obtained the product as a yellow oil.

EXAMPLE 34

Methyl [p-(α,α,α-trifluoro-m-tolyloxy)phenyl]acetate

A solution of 73.5 ml of 70% perchloric acid in 370 ml of methanol is cooled to 0° C. and 73.76 g of thallium nitrate trihydrate followed by 42.25 g of 4'-(α,α,α-trifluoro-m-tolyloxy)acetophenone are added. The mixture is allowed to stir overnight while warming to room temperature. A white solid is removed by filtration and the filtrate is diluted with one liter of water. The resulting mixture is extracted with three 200 ml portions of chloroform. The combined organic extracts are washed with two 200 ml portions of water, 200 ml of saturated NaHCO₃, saturated NaCl and dried over MgSO₄. Evaporation of the solvent affords a yellow oil, which is filtered through aluminum oxide (benzene) and distilled at 0.07 mm to give the product as a yellow oil, bp 120°–148° C.

EXAMPLE 35

[p-(α,α,α-Trifluoro-m-tolyloxy)phenyl]acetic Acid

A mixture of 12.40 g of methyl [p-(α,α,α-trifluoro-m-tolyloxy)phenyl]acetate, 30 ml of 20% KOH and 10 ml of water is refluxed overnight. After dilution with 250 ml of water, the clear orange solution is acidified and extracted with two 50 ml portions of chloroform. The combined organic extracts are washed with two 50 ml portions of water, saturated brine, and dried over MgSO₄. Evaporation of the solvent affords white crystals, mp 61°–63° C. (from petroleum ether). Recrystallization from petroleum ether affords colorless blades, mp 61°–62.5° C.

EXAMPLE 36

Methyl α-(phenoxy)-α-[p-(p-chlorophenylthio)phenyl]acetate

A mixture of 5.0 g of methyl α-(phenoxy)-α-(p-iodophenyl)acetate and 3.09 g of cuprous 4-chlorophenylmercaptide in 150 ml of pyridine is heated under Argon overnight. The resulting brown solution is added to 300 ml of water and extracted with 2×100 ml of chloroform. The extracts are washed with two 50 ml portions of 10% HCl, 50 ml H₂O, 50 ml 5% NaOH, 50 ml saturated NaHCO₃, 150 ml of saturated brine and dried over MgSO₄. Evaporation of the solvent yields a brown oil which is filtered through aluminum oxide (benzene). The resulting amber oil is purified by chromatography on 25 g of silica gel (benzene) and bulb-to-bulb distillation (176° C. @ 0.075 mm) to give the product as a yellow oil.

EXAMPLE 37

Methyl [p-(p-chlorophenylsulfonyl)phenyl]acetate

A mixture of 14.62 g of methyl [p-(p-chlorophenylthio)phenyl]acetate, 100 ml of glacial acetic acid and 62.5 ml of 30% hydrogen peroxide is heated to 70° C. and kept at 70° C. for 3 hours. After cooling, the mixture is poured into 500 ml of water and extracted with three 100 ml portions of chloroform. The combined extracts are washed with three 100 ml portions of water, 100 ml of saturated NaHCO₃, saturated brine and dried over MgSO₄. Evaporation of the solvent affords an oil which crystallizes on standing to give 14.9 g of product as white crystals (from petroleum ether) mp 78°–80° C.

EXAMPLE 38

4'-(4-chloro-1-naphthyloxy)acetophenone

A mixture of 35.6 g of 4-chloro-1-naphthol, 27.62 g of 4-fluoroacetophenone, and 55.2 g of potassium carbonate in 250 ml of N,N-dimethylacetamide are heated under Argon with vigorous stirring at 150°–155° C. overnight. After cooling to room temperature, 500 ml of water is added and the mixture is extracted with three 150 ml portions of benzene. The combined extracts are washed with two 150 ml portions of 5% NaOH, three 150 ml portions of 10% HCl, two 150 ml portions of water, 150 ml of saturated NaHCO$_3$, 150 ml of saturated brine, and dried over MgSO$_4$. Evaporation of the solvent at reduced pressure affords a light brown solid, which is extracted with 800 ml of hot hexane to give the product as a tan solid, mp 98°–105° C. Recrystallization from 15:1 hexane-chloroform gives cream colored plates, mp 100°–104.5° C.

EXAMPLE 39

Methyl α-(p-tert-butylphenoxy)-α-[p-(4-chlorophenoxy)phenyl]acetate

To a solution of 3.75 g of 4-tert-butylphenol and 1.19 g of sodium methoxide and a few crystals of potassium iodide in 40 ml of methanol is added 7.11 g of methyl α-bromo-α-[p-(p-chlorophenoxy)phenyl]acetate in 10 ml of benzene. The mixture is refluxed overnight. On cooling, a white solid separates. The entire mixture is poured into 100 ml of water and extracted with two 100 ml portions of ether. The combined extracts are washed with 100 ml of 5% NaOH, 100 ml of water and saturated brine, and dried over MgSO$_4$. Evaporation of the solvent affords a white solid, which is crystallized from hexane to give the product as fine white needles, mp 118°–120° C.

EXAMPLE 40

Methyl α-(m-tert-butylphenoxy)-α-[p-(p-chlorophenoxy)phenyl]acetate

In an identical manner as in Example 39, 7.11 g of methyl α-bromo-α-[p-(p-chlorophenoxy)phenyl]acetate is reacted with 3.75 g of 3-tert-butylphenol in methanol to give a yellow oil. Fractional bulb-to-bulb distillation gives the product as a viscous yellow oil (182° C. @ 0.05 mm).

EXAMPLE 41

Methyl α-[p-(p-chlorophenoxy)phenyl]-α-(α,α,α-trifluoro-m-tolyloxy)acetate

In a similar manner as in Example 39, 7.11 g of methyl α-bromo-α-[p-(p-chlorophenoxy)phenyl]acetate is reacted with 4.05 g of m-hydroxybenzotrifluoride in methanol to give a yellow oil which is purified by fractional bulb-to-bulb distillation to give the product as a colorless oil (172° C. @ 0.05 mm).

EXAMPLE 42

Methyl (3-biphenylyloxy)[p-(p-chlorophenoxy)phenyl]acetate

In a similar manner as in Example 39, 7.11 g of methyl α-bromo-α-[p-(p-chlorophenoxy)phenyl]acetate is reacted with 4.25 g of 3-phenylphenol in methanol to give a yellow oil, which is subjected to fractional bulb-to-bulb distillation (175°–178° C. @ 0.02 mm) to remove volatile impurities. The glassy residue is subjected to filtration through 200 g of silica gel (benzene) and concentration to yield the product as an orange foam.

EXAMPLE 43

Methyl α-(4-chloro-1-naphthyloxy)-α-[p-(p-chlorophenoxy)phenyl]acetate

In a similar manner as in Example 39, 7.11 g of methyl α-bromo-α-[p-(p-chlorophenoxy)phenyl]acetate is reacted with 4.46 g of 4-chloro-1-naphthol in methanol to give a brown oil which is subjected to column chromatography on 250 g of silica gel. Elution with benzene affords, after 500 ml, two fractions (250 ml of eluant) which yields the product as a white solid (mp 94°–96° C.) after tritration with petroleum ether. A sample is recrystallized from 10 ml of hexane to yield white crystals, mp 94°–96° C.

EXAMPLE 44

Methyl α-(p-acetamidophenoxy)-α-[p-(p-chlorophenoxy)phenyl]acetate

To a solution of 3.78 g of p-acetamidophenol, 1.1 g of sodium methoxide, and 50 mg of potassium iodide in 40 ml of methanol is added 7.11 g of methyl α-bromo-α-[p-(p-chlorophenoxy)phenyl]acetate in 15 ml of benzene. The mixture is refluxed for 20 hours, poured into ice and water and extracted with chloroform. The chloroform extracts are washed with 10% potassium carbonate and with water. The extract is dried over magnesium sulfate and concentrated to a gum under vacuum. Petroleum ether is added to the residue and several ml of acetone. Scratching the flask gives crystals which are filtered to give the product as pink crystals, mp 152°–157° C. The crystals are dissolved in a minimum amount of hot acetone, the solution chilled and diluted with petroleum ether. Chilling and filtering gives pale pink crystals mp 157°–160° C.

EXAMPLE 45

Methyl (m-[m-phenoxyphenoxy]phenoxy)-α-[p-(p-chlorophenoxy)phenyl]acetate

To a solution of 6.96 g of m-(m-phenoxyphenoxy)phenol, 1.19 g of sodium methoxide and 50 mg of potassium iodide in 40 ml of methanol is added 7.11 g of methyl α-bromo-α-[p-(p-chlorophenoxy)phenyl]acetate in 10 ml of benzene. The mixture is refluxed for 20 hours, poured into ice and water and extracted with chloroform. The chloroform extracts are washed with 10% potassium carbonate and with water. The extract is dried over magnesium sulfate and concentrated under vacuum to give an oil. Filtration once through silica gel (chloroform solvent) and again through silica gel with benzene as solvent gives the product as an oil.

EXAMPLE 46

Methyl α-(p-chlorophenoxy)-α-[p-(p-cyanophenoxy)phenyl]acetate

To a solution of 40 ml of methanol, 1.19 g of sodium methoxide and 3.21 g of p-chlorophenol is added 7.4 g of methyl α-bromo-α-[p-(p-cyanophenoxy)phenyl]acetate in 15 ml of benzene. The mixture is refluxed for 20 hours, poured into ice and water, and extracted with ether. The ether extracts are washed with 10% potassium carbonate and with water. Drying over magnesium sulfate and removal of the solvent under vacuum gives a tan oil. Filtration once through silica gel with chloroform as solvent gives an oil in the first fractions. The oil is filtered through silica gel with benzene as the solvent to give, in the first fractions, a pale yellow oil.

EXAMPLE 47

α-(p-Fluorophenoxy)-α-[p-(p-chlorophenoxy)phenyl]acetic acid

To a solution of 2.80 g of p-fluorophenol and 1.19 g of sodium methoxide in 40 ml of methanol is added 50 mg of potassium iodide and 7.11 g of methyl α-bromo-α-[p-(p-chlorophenoxy)phenyl]acetate in 10 ml of benzene. The mixture is refluxed for 20 hours and the solvent removed under vacuum. To the residue is added water and the mixture is extracted with ether. The ether extracts are washed with 10% potassium carbonate and with water and dried (MgSO$_4$). The solvent is removed under vacuum to give a tan oil. The oil is dissolved in 60 ml. of ethanol and 6 ml of water and 5 g of potassium hydroxide is added. The mixture is refluxed for 3.5 hours, acidified with concentrated hydrochloric acid, diluted with water and poured onto ice. The mixture is extracted with chloroform and the extracts washed with water and dried over magnesium sulfate. Concentration in vacuo gives an oil. The oil is dissolved in aqueous sodium bicarbonate and the mixture extracted with chloroform. The aqueous layer is acidified with concentrated hydrochloric acid, extracted with ether and the extracts dried (MgSO$_4$). Removal of the solvent in vacuo gives the product as a tan oil. A small sample is crystallized, mp 106°–111° C.

EXAMPLE 48

Methyl α-(3,4,5-trichlorophenoxy)-α-[p-(p-chlorophenoxy)phenyl]acetate

To a solution of 4.93 g of 3,4,5-trichlorophenol and 1.19 g of sodium methoxide in 40 ml of methanol is added 7.11 g of methyl α-bromo-α-[p-(p-chlorophenoxy)phenyl]acetate in 10 ml of benzene and 50 mg of potassium iodide. The mixture is refluxed for 20 hours and the solvent removed in vacuo. To the residue is added water and the mixture is extracted with ether. The ether extracts are washed with 10% potassium carbonate and with water and dried (MgSO$_4$). Evaporation of the solvent under vacuum gives a tan oil. The oil is dissolved in chloroform and filtered through a column of silica gel. Removal of the solvent from the second 200 ml cut gives the product as a tan oil.

EXAMPLE 49

α-[p-(p-Phenoxy)phenoxy]-α-[p-(p-chlorophenoxy)phenyl]acetic acid

To a solution of 4.66 g of p-phenoxyphenol and 1.19 g of sodium methoxide in 40 ml of methanol is added 7.11 g of methyl α-bromo-α-[p-(p-chlorophenoxy)phenyl]acetate in 10 ml of benzene and 50 mg of potassium iodide. The mixture is refluxed for 22 hours and poured into ice and water. The mixture is extracted with ether and the ether extracts washed with 10% potassium carbonate and with water. The extracts are dried over magnesium sulfate and concentrated under vacuum to give a tan oil. The oil is combined with 60 ml of ethanol, 6 ml of water and 5 g of potassium hydroxide and the mixture is refluxed for 3.5 hours. The mixture is acidified with concentrated hydrochloric acid, diluted with water and extracted with chloroform. The chloroform extracts are dried (MgSO$_4$) and concentrated under vacuum to give an oil. The oil is dissolved in methanol, filtered through Celite and the filtrate concentrated under vacuum to an oil. The oil is heated overnight on a steam bath under vacuum (0.1 mmm) to give the product as a thick oil.

EXAMPLE 50

Methyl α-[p-(Benzyloxy)phenoxy]-α-[p-(p-chlorophenoxy)phenyl]acetate

To a solution of 5.0 g of p-benzyloxyphenol and 1.19 g of sodium methoxide in 40 ml of methanol is added 50 mg of potassium iodide and 7.11 g of methyl α-bromo-α-[p-(p-chlorophenoxy)phenyl]acetate in 10 ml of benzene. The mixture is refluxed for 22 hours and poured into ice and water. The mixture is extracted with ether and the ether extracts washed with 10% potassium carbonate and with water. The extracts are dried (MgSO$_4$) and the solvent removed under vacuum to give an oily solid. Trituration with hexane plus a small amount of acetone and chilling gives crystals. Filtration gives the product as off-white crystals, mp 91°–96° C. Recrystallization by dissolving in hot acetone, diluting with petroleum ether, chilling and filtering gives the product as white crystals, mp 88°–90° C.

EXAMPLE 51

Methyl α-(m-chlorophenoxy)-α-[p-(p-chlorophenoxy)phenyl]acetate

To a solution of 1.19 g of sodium methoxide and 3.21 g of m-chlorophenol in 40 ml of methanol is added 50 mg of potassium iodide and 7.11 g of methyl α-bromo-α-[p-(p-chlorophenoxy)phenyl]acetate in 10 ml of benzene. The mixture is refluxed overnight and poured into 100 ml of water. The mixture is extracted with ether and the ether extracts washed with 5% NaOH, water, saturated NaCl solution and dried (MgSO$_4$). The solvent is removed under vacuum to give an oil. Chromatography over silica gel (solvent-benzene) gives the product as a pale yellow oil.

EXAMPLE 52

Methyl α-(p-cyclohexylphenoxy)-α-[p-(p-chlorophenoxy)phenyl]acetate

To a solution of 1.19 g of sodium methoxide and 4.4 g of p-cyclohexylphenol in 40 ml of methanol is added 50 mg of potassium iodide and 7.11 g of methyl α-bromo-α-[p-(p-chlorophenoxy)phenyl]acetate in 10 ml of benzene. The solution is refluxed overnight, cooled to room temperature and poured into 100 ml of water. The mixture is extracted with two 60 ml portions of ether and the combined extracts washed with two 50 ml portions of 5% sodium hydroxide, 50 ml of water and 50 ml of saturated NaCl. The extract is dried (MgSO$_4$) and the solvent removed under vacuum. The residue is triturated with petroleum ether to give the product as white crystals, mp 122°–123.5° C.

EXAMPLE 53

Methyl α-(3,5-dimethyl-4-chlorophenoxy)-α-[p-(p-chlorophenoxy)phenyl]acetate

To a solution of 1.19 g of sodium methoxide and 50 mg of potassium iodide in 40 ml of methanol is added 3.92 g of 3,5-dimethyl-4-chlorophenol. After one hour, a solution of 7.11 g of methyl α-bromo-α-[p-(p-chlorophenoxy)phenyl]acetate in 10 ml of benzene is added. The solution is refluxed overnight. After cooling to room temperature the mixture is poured into 100 ml of water and extracted with two 60 ml portions of ether. The combined extracts are washed with two 50 ml portions of 5% NaOH, 50 ml of water, 50 ml of saturated brine and dried (MgSO$_4$). Evaporation of the solvent affords a yellow oil which is chromatographed on 100 g silica gel and eluted with 400 ml of benzene. Evaporation of the solvent under vacuum gives the product as a colorless oil.

EXAMPLE 54

Methyl (p-chlorophenoxy)[p-(p-chlorophenylsulfinyl)phenyl]acetate

To a solution of 1,8 g of methyl (p-chlorophenoxy)[p-(p-chlorophenylthio)phenyl]acetate in 10 ml of dichloromethane is added dropwise a solution of 0.891 g of 83% m-chloroperbenzoic acid in 10 ml of dichloromethane. The mixture is chilled overnight, filtered and the filtrate washed with 10% sodium sulfite solution, saturated sodium bicarbonate and sodium chloride solutions. After drying (MgSO$_4$), the solvent is removed under reduced pressure to give a gum. Crystallization from dichloromethane-zepane given 1.65 g of product as white crystals, mp 134°–144° C.

EXAMPLE 55

Methyl 2-(p-chlorophenoxy)-2-[p-(p-chlorophenoxy)phenyl]-propionate

A solution of 2.02 g of N,N-diisopropylamine and 5 mg of 1,10-phenanthroline in 15 ml of dry tetrahydrofuran is cooled to 0° C. under argon and a solution of 0.017 mole of n-butyllithium in hexane is added dropwise while keeping the temperature of 0°–5° C. After 15 minutes, the solution is cooled to −70° C. and a solution of 6.05 g of methyl(p-chlorophenoxy)[p-(p-chlorophenoxy)phenyl]acetate in 10 ml of tetrahydrofuran is added over 15 minutes while keeping the temperature at −70° C. to −65° C. After 15 minutes 3.58 g of hexamethylphosphoramide is added. After ½ hour, 4.26 g of methyl iodide is added in one portion. The color lightens slowly over one hour. The mixture is allowed to warm to room temperature and the reaction mixture is stirred overnight. The mixture is poured into 100 ml of water and extracted with two 75 ml portions of ether. The extracts are washed with four 50 ml portions of 10% HCl, water, saturated NaHCO$_3$, saturated brine and dried (MgSO$_4$). Evaporation of the solvent yields a brown oil, which is filtered through 30 g of silica gel (benzene eluent) to yield the product as a light yellow oil, which solidifies on standing.

EXAMPLE 56

Methyl (p-tert-butylphenoxy[p-(p-acetamidophenoxy)phenyl]acetate

To a suspension of 6.5 g of methyl α-(p-tert-butylphenoxy)α-[p-(p-nitrophenoxy)phenyl]acetate in 150 ml of methanol is added 500 mg of 10% palladium on carbon and the mixture hydrogenated with shaking. The mixture is cooled, filtered and the solvent removed under reduced pressure to give a gum. The gum is dissolved in 10 ml of pyridine and 3.0 ml of acetic anhydride added. After standing at room temperature for 18 hours the mixture is poured into 100 ml of ice-water. The gum which forms is separated, dissolved in dichloromethane and washed with dilute hydrochloric acid, sodium bicarbonate solution and with sodium chloride solution. The solvent is removed under reduced pressure to give a gum which is crystallized from ether to give 5.3 g of white crystals, mp 141°–143° C.

EXAMPLE 57

Ethyl α-[p-(p-cyanophenoxy)phenyl]acetate

A mixture of 2.21 g of p-fluorobenzonitrile, 2.16 g of ethyl p-hydroxyphenylacetate and 2.07 g of K$_2$CO$_3$ in 20 ml of N,N-dimethylacetamide is stirred and heated at 155° C. for 18 hours. The mixture is chilled and poured into 40 ml of cold saturated NaHCO$_3$ solution. The mixture is extracted with ether and the extracts washed with cold 2 N NaOH and saline. The extracts are dried (MgSO$_4$) and concentrated under vacuum to give the product as a yellow oil.

EXAMPLE 58

Ethyl α-bromo-α-[p-(p-cyanophenoxy)phenyl]acetate

To a solution of 1.17 g of ethyl[p-(p-cyanophenoxy)phenyl]acetate in 20 ml of carbon tetrachloride is added 0.75 g of N-bromosuccinimide and a drop of 48% HBr. The mixture is stirred and refluxed for 42 hours. The solvent is removed under vacuum to give the product.

EXAMPLE 59

Methyl α-bromo-α-[p-(p-cyanophenoxy)phenyl]acetate

To a solution of 16.0 g of crystalline methyl α-[p-(p-cyanophenoxy)phenyl]acetate in 300 ml of carbon tetrachloride is added 12.5 ml of N-bromosuccinimide and 1 drop of 48% hydrogen bromide. After stirring and refluxing for 22 hours, 3 drops of 48% HBr are added and after refluxing 46 hours, 50 mg of benzoyl peroxide is added. The mixture is refluxed for 3 hours and one inch of 22 gauge nichrome wire is added. After refluxing an additional 18 hours, the mixture is irradiated with two 50 watt fluorescent bulbs while refluxing for 24 hours. To complete the reaction several drops of bromine are added and the mixture is refluxed for 3 days. The mixture is filtered and to the filtrate is added 2.5 g of N-bromosuccinimide. The mixture is refluxed for 48 hours. The mixture is passed through a column of silica gel and eluted with carbon tetrachloride and with benzene. From the cuts containing the product there is obtained crystals, mp 60°–63° C. (from CCl$_4$-petroleum ether).

EXAMPLE 60

Methyl [p-(p-cyanophenoxy)phenyl]acetate

A solution of 22.25 g of [p-(p-cyanophenoxy)phenyl]acetic acid in 55 ml of thionyl chloride is refluxed for one hour. The solvent is removed under vacuum, benzene is added (three times) and the solvent removed under vacuum. The residue is dissolved in 135 ml of methanol and stirred at room temperature for 1 hour. The solvent is removed under vacuum to give a gum. The gum is dissolved in 50 ml of warm methanol and the solution is chilled and filtered to give the product, mp 58°–60° C.

EXAMPLE 61

Methyl α-bromo-α-[p-(p-methylsulfonylphenoxy)phenyl]acetate

To a suspension of 1.6 g of methyl α-[p-(p-methylsulfonylphenoxy)phenyl]acetate in 25 ml of carbon tetrachloride is added 0.98 g of N-bromosuccinimide and 1 drop of 48% HBr. The mixture is stirred and refluxed for 19.5 hours and 10 mg of benzoyl peroxide is added. The mixture is refluxed for 3 hours and ½ inch of 22 gauge nichrome wire is added. After refluxing an additional 18 hours the solvent is removed under vacuum to give the product as a gum.

EXAMPLE 62

Methyl-α-(p-fluorophenoxy)[p-(p-chlorophenoxy)phenyl]acetate

To a solution of 1.87 g of p-fluorophenol in 50 ml of methanol is added 1.07 g of sodium methoxide. To this solution is added 5.4 g of methyl α-bromo-α-[p-(p-chlorophenoxy)phenyl]acetate and the mixture is refluxed for 18 hours. The mixture is concentrated to ½ volume and poured into 150 ml of ice and water. The mixture is extracted with ether and the cold extracts washed with 50 ml of 2 N NaOH and with saline. After drying (MgSO₄), the extracts are concentrated under vacuum to give the product as an amber colored oil.

EXAMPLE 63

Methyl [p-(p-methylsulfonylphenoxy)phenyl]acetate

A solution of 14.2 g of [p-(p-methylsulfonylphenoxy)phenyl]acetic acid in 28 ml of thionyl chloride is refluxed for one hour. The solvent is removed under vacuum, benzene is added several times and the solvent removed under vacuum. To the residue is added 70 ml of methanol and the mixture is stirred at room temperature for one hour. The solvent is removed under vacuum and the residue triturated with 35 ml of ether. The mixture is filtered and the solid washed with 15 ml of ether and with petroleum ether (bp 30°–60° C.) to give tan crystals, mp 93°–98° C. Recrystallization from dichloromethane-petroleum ether (bp 30°–60° C.) gives the product as tan crystals, mp 100°–102° C.

EXAMPLE 64

Methyl α-(p-chlorophenoxy)-α-[p-(p-methylsulfonylphenoxy)phenyl]acetate

To a solution of 1.38 g of p-chlorophenol and 0.585 g of sodium methoxide in 10 ml of methanol is added a solution of 3.53 g of methyl α-bromo-α-[p-(p-methylsulfonylphenoxy)phenyl]acetate in 15 ml of methanol. The mixture is refluxed for 20 hours, chilled and filtered to give 2.71 g of white crystals, mp 182°–183° C. Recrystallization by heating in 75 ml of acetone and adding 20 ml of dichloromethane, followed by adding hexane gives on chilling the product as white crystals, mp 182°–183° C.

EXAMPLE 65

[p-(p-Cyanophenoxy)phenyl]acetic acid

A mixture of 17.4 g of p-fluorobenzonitrile, 31.0 g of ethyl p-hydroxyphenylacetate, 23.8 g of potassium carbonate and 175 ml of N,N-dimethylacetamide is heated at 158° C. for 18 hours. The mixture is cooled and poured into 300 ml of cold sodium bicarbonate solution. The mixture is extracted with ether and the ether extracts washed with two 200 ml portions of 2 N NaOH. The aqueous solutions are saturated with salt and extracted with ether. The alkaline aqueous layer is acidified with cold hydrochloric acid to give a solid which is filtered and washed with water to give tan crystals. Recrystallization by dissolving in 300 ml of methanol, adding 200 ml of water and chilling gives the product as yellow needles, mp 125°–127° C.

EXAMPLE 66

Methyl α-(α,α,α-triluoro-m-tolyloxy)-α-[p-(p-cyanophenoxy)phenyl]acetate

To a solution of 3.16 g of m-hydroxybenzotrifluoride and 1.07 g of sodium methoxide in 50 ml of methanol is added 5.4 g of methyl α-bromo-α-[p-(p-cyanophenoxy)phenyl]acetate. The mixture is refluxed for 18 hours and concentrated to ½ volume under vacuum. The mixture is poured into 150 ml of ice and water and extracted with ether. The cold ether extracts are washed with 50 ml of 2 N NaOH and with saline and dried (MgSO₄). Evaporation of the solvent under vacuum gives the product as an amber oil.

EXAMPLE 67

Methyl α-bromo-α-[p-(p-methylsulfonylphenoxy)phenyl]acetate

To a mixture of 0.80 g of methyl α-[p-(p-methylsulfonylphenoxy)phenyl]acetate and 0.49 g of N-bromosuccinimide in 12.5 ml of carbon tetrachloride is added several drops of carbon tetrachloride containing bromine. The mixture is stirred and refluxed for 3 days and the solvent removed under vacuum. The residue is dissolved in dichloromethane and filtered through a one inch by five inch column of silica gel. Evaporation of the filtrate gives the product as an oil.

EXAMPLE 68

Methyl α-(3,4-dichlorophenoxy)-α-[p-(p-chlorophenoxy)phenyl]acetate

To a solution of 4.08 g of 3,4-dichlorophenyl, 1.188 g of sodium methoxide, and 50 mg of potassium iodide in 40 ml of methanol is added 7.11 g of methyl α-bromo-α-[p-(p-chlorophenoxy)phenyl]acetate in 10 ml of benzene. The mixture is maintained at reflux overnight and then poured into 100 ml of water. The product is extracted with ether and the extracts are washed with 5% NaOH, water and brine and dried (MgSO₄). Evaporation of the solvent yields an oil which is chromatographed on 100 g of silica gel (benzene 400 ml) to yield a yellow oil.

EXAMPLE 69

Methyl α-(2-chloro-4-tert-butylphenoxy)-α-[p-(p-chlorophenoxy)phenyl]acetate

To a solution of 4.62 g of 2-chloro-4-tert-butylphenol, 1.188 g of sodium methoxide and 50 mg of potassium iodide in 40 ml of methanol is added 7.11 g of methyl α-bromo-α-[p-(p-chlorophenoxy)phenyl]acetate in 10 ml of benzene. The mixture is heated at reflux overnight. The mixture is worked up as described in Example 68 to yield a yellow oil. Chromatography on 100 g of silica gel (benzene, 400 ml) affords an oil which solidifies. Recrystallization from hexane yields white plates, mp 85.5°–88° C.

EXAMPLE 70

Methyl α-(3,5-dichlorophenoxy-α-[p-(p-chlorophenoxy)phenyl]acetate

To a solution of 4.08 g of 3,5-dichlorophenol, 1.188 g of sodium methoxide, and 50 mg of potassium iodide in 40 ml of methanol is added 7.11 g of methyl α-bromo-α-[p-(p-chlorophenoxy)phenyl]acetate in 10 ml of benzene. The mixture is maintained at reflux overnight and then added to 100 ml of water. The product is then extracted with ether, and the ether is washed with 5% sodium hydroxide, water, brin and dried (MgSO₄). Evaporation of the solvent yields an oil which is chromatographed on 100 g of silica gel (benzene, 400 ml) to yield a yellow oil.

EXAMPLE 71

Methyl α-(3,5-di-tert-butylphenoxy)-α-[p-(p-chlorophenoxy)-phenyl]acetate

To a solution of 5.16 g of 3,5-di-tert-butylphenol 1.188 g of sodium methoxide, and 50 mg of potassium iodide in 40 ml of methanol is added 7.11 g of methyl α-bromo-α-[p-(p-chlorophenoxy)phenyl]acetate in 10 ml of benzene. The solution is heated at reflux overnight and worked up as described in Example 70 to yield a yellos oil which is purified by chromatography on 100 of silica gel (benzene, 400 ml) and pumped in vacuo at 120° C. (0.05 mm) to yield a yellow glass.

EXAMPLE 72

(p-Chlorophenoxy)[p-(p-chlorophenoxy)phenyl]acetic acid

To a solution of 10 g of KOH in 80 ml of 50% methanol is added 30.2 g of methyl (p-chlorophenoxy)-[p-(p-chlorophenoxy)phenyl]acetate. The mixture is refluxed for 3 hours, cooled, poured into 100 ml of water. The solution is extracted with two 100-ml portions of ether. The aqueous layer is acidified with concentrated hydrochloric acid. The mixture is extracted with two 100-ml portions of ether and the extracts are washed with water, brine and dried (MgSO₄). Evaporation of the solvent yields an oil which is triturated with petroleum ether to give 27.5 g of product as white crystals. Recrystallization from hexane-chloroform gives white plates, mp 141°–142° C.

EXAMPLE 73

Methyl α-(4-indanyloxy)-α-[p-(p-chlorophenoxy)phenyl]acetate

To a solution of 3.36 g of 4-indanol, 1.188 g of sodium methoxide and 50 mg of potassium iodide in 40 ml of methanol is added 7.11 g of methyl α-bromo-α-[p-(p-chlorophenoxy)phenyl]acetate in 10 ml of benzene. The mixture is refluxed overnight and then poured into 100 ml of water. The mixture is extracted with 2×75 ml of ether. The combined extracts are washed with 50 ml of 5% NaOH, 50 ml of water, 50 ml saturated brine, and dried (MgSO₄). Evaporation of the solvent yields a yellow oil. Chromatography on 100 g of silica gel (benzene, 400 ml) yields the product as a light yellow oil which solidifies on standing.

EXAMPLE 74

Methyl α-(4-chloro-3-methylphenoxy)-α-[p-(p-chlorophenoxy)phenyl]acetate

To a solution of 3.565 g of 4-chloro-3-methylphenol, 1.188 g of sodium methoxide and 50 mg of potassium iodide in 40 ml of methanol is added 7.11 g of methyl α-bromo-α-[p-(p-chlorophenoxy)phenyl]acetate in 10 ml of benzene. The mixture is refluxed overnight and poured into 100 ml of water. The mixture is extracted with 2×75 ml of ether and the combined extracts are washed with 50 ml of 5% NaOH, 50 ml of water, 50 ml of saturated brine and dried (MgSO₄). Evaporation of the solvent yields a yellow oil. Chromatography on 100 g of silica gel yields a colorless oil.

EXAMPLE 75

Methyl α-(3,4-dimethylphenoxy)-α-[p-(p-chlorophenoxy)phenyl]acetate

To a solution of 3.055 g of 3,4-dimethylphenol, 1.188 g of sodium methoxide and 50 mg of potassium iodide in 40 ml of methanol is added 7.11 g of methyl α-bromo-α-[p-(p-chlorophenoxy)phenyl)]acetate in 10 ml of benzene. The mixture is refluxed overnight. After cooling to room temperature, the mixture is poured into 100 ml of water and extracted with 2×75 ml of ether. The combined extracts are washed with 50 ml of 5% NaOH, 50 ml of water, 50 ml of saturated brine and dried (MgSO₄). Evaporation of the solvent yields a yellow oil. Chromatography on 100 g of silica gel (benzene, 400 ml) yields the product as a yellow oil.

EXAMPLE 76

Methyl α-(5,6,7,8-tetrahydro-1-naphthoxy)-α-[p-(p-chlorophenoxy)phenyl]acetate

To a solution of 3.70 g of 5,6,7,8-tetrahydro-1-naphthol, 1.188 g of sodium methoxide and 50 mg of potassium iodide in 40 ml of methanol is added 7.11 g of methyl α-bromo-α-[p-(p-chlorophenoxy)phenyl]acetate in 10 ml of benzene. The mixture is refluxed overnight. After cooling to room temperature, the mixture is extracted with 2×75 ml of ether. the combined extracts are washed with 50 ml of 5% NaOH, 50 ml of water, 50 ml of saturated brine and dried (MgSO₄). Evaporation of the solvent yields a yellow oil. Chromatography on 100 g of silica gel (benzene, 400 ml) yields the product as a yellow oil.

EXAMPLE 77

Methyl α-(1-naphthoxy)-α-[p-(p-chlorophenoxy)phenyl]acetate

To a solution of 3.60 g of 1-naphthol, 1.188 g of sodium methoxide and 50 mg of potassium iodide in 40 ml of methanol is added 7.11 g of methyl α-bromo-α-[p-(p-chlorophenoxy)phenyl]acetate in 10 ml of benzene. The solution is refluxed overnight and then poured into 100 ml of water. The mixture is extracted with 2×75 ml of ether. The combined extracts are washed with 2×50 ml of 5% NaOH, 50 ml of water, saturated brine and dried (MgSO$_4$). Evaporation of the solvent yields a red oil. Chromatography on 100 g of silica gel (benzene, 400 ml) affords a pink oil which solidifies on trituration with petroleum ether to yield a pink solid, mp 107°–109.5° C.

EXAMPLE 78

Methyl α-bromo-α-[p-(p-methylsulfonylphenoxy)phenyl]acetate

A solution of 3.06 g of [p-(p-methylsulfonylphenoxy)phenyl]acetic acid and 6 ml of thionyl chloride is refluxed for one hour. The solvent is removed under vacuum and benzene added several times and removed under vacuum. The residue is suspended in carbon tetrachloride and 1.96 g of N-bromosuccinimide is added. The mixture is refluxed for 5.5 hours. Methanol is added and the mixture refluxed for ½ hour. The solvent is removed under vacuum and the residue dissolved in dichloromethane and passed through a one inch by twelve inch column of silica gel. The first three cuts (100 ml) give, on removal of the solvent, the product as an oil.

EXAMPLE 79

Methyl α-(5-indanyloxy)-α-[p-(p-chlorophenoxy)phenyl]acetate

To a solution of 3.36 g of 5-indanol, 1.19 g of sodium methoxide and 50 mg of potassium iodide in 40 ml of methanol is added 7.11 g of methyl α-bromo-α-[p-(p-chlorophenoxy)phenyl]acetate in 10 ml of benzene. The mixture is refluxed overnight and added to 100 ml of water. The mixture is then extracted with 2×75 ml of ether and the combined extracts are washed with 50 ml of 5% NaOH, 50 ml of water, 50 ml of saturated brine and dried (MgSO$_4$). Evaporation of the solvent yields a yellow oil. Chromatography on 100 g of silica gel (benzene, 400 ml) yields a light yellow oil.

EXAMPLE 80

Methyl α-(2-naphthyloxy)-α-[p-(p-chlorophenoxy)phenyl]acetate

To a solution of 3.60 g of 2-naphthol, 1.19 g of sodium methoxide and 50 mg of potassium iodide is added 7.11 g of methyl α-bromo-α-[p-(p-chlorophenoxy)phenyl]acetate in 10 ml of benzene. The solution is maintained at reflux overnight and then poured into 100 ml of water. The mixture is then extracted with 2×75 ml of ether and the combined extracts are washed with 2×50 ml of 5% NaOH, 50 ml of water, 50 ml of saturated brine and dried (MgSO$_4$). Evaporation of the solvent yields a yellow oil. Chromatography on 100 g of silica gel (benzene, 400 ml) yields a green glass. Further elution with 200 ml of benzene yields the product as a glass.

EXAMPLE 81

(2,3-dihydroxy)propyl(p-chlorophenoxy)[p-(p-chlorophenoxy)phenyl]acetate

A mixture of 8.22 g of sodium (p-chlorophenoxy)[p-(p-chlorophenoxy)-phenyl]acetate, 3.3 g of 1-chloro-2,3-propanediol and 3.3 g of potassium iodide in 120 ml of N,N-dimethylacetamide is heated under argon at 130°–135° C. for 7 hours. The mixture is cooled and added to 1 liter of water, which causes as oil to separate. The mixture is extracted with three 200-ml portions of ether. The combined extracts are washed with 100 ml of 5% NaOH, 100 ml of water and 100 ml of saturated brine and dried. The solvent is evaporated and the residual is placed on a column containing 100 g of silica gel. After several washes with chloroform, the purified product was eluted with ether to give 5.4 g of the product as an oil.

EXAMPLE 82

Methyl α-(5,6,7,8-tetrahydro-2-naphthyloxy)-α-[p-(p-chlorophenoxy)phenyl]acetate To a solution of 3.70 g of 5,6,7,8-tetrahydro-2-naphthol, 1.19 g of sodium methoxide and 50 mg of potassium iodide in 40 ml of methanol is added 7.11 g of methyl α-bromo-α-[p-(p-chlorophenoxy)phenyl]acetate in 40 ml of benzene. The mixture is maintained at reflux overnight and then poured into 100 ml of water. The mixture is then extracted with 2×75 ml of ether. The combined extracts are washed with 2×50 ml of 5% NaOH, 50 ml of water, 50 ml of saturated brine and dried (MgSO$_4$). Evaporation of the solvent yields a yellow oil. Chromatography on 100 g of silica gel yields a yellow oil.

EXAMPLE 83

Methyl α-(α,α,α-trifluoro-p-tolyloxy)-α-[p-(p-chlorophenoxy)phenyl]acetate

To a solution of 4.08 g of α,α,α-trifluoro-p-cresol, 1.19 g of sodium methoxide and 50 mg of potassium iodide in 40 ml of methanol is added 7.11 g of methyl α-bromo-α-[p-(p-chlorophenoxy)phenyl]acetate in 10 ml of benzene. The mixture is refluxed overnight and then poured into 100 ml of water. The mixture is then extracted with 2×75 ml of ether. The combined extracts are washed with 2×50 ml of 5% NaOH, 50 ml of water, 50 ml of saturated brine and dried (MgSO$_4$). Evaporation of the solvent yields a yellow oil. Chromatography on 100 g of silica gel (benzene, 400 ml) affords the product as a colorless oil.

EXAMPLE 84

Methyl α-[p-(1-adamantyl)phenoxy]-α-[p-(p-chlorophenoxy)phenyl]acetate

To a solution of 5.7 g of p-(1-adamantyl)phenol, 1.19 g of sodium methoxide and 50 mg of potassium iodide in 40 ml of methanol is added 7.11 g of methyl α-bromo-α-[p-(p-chlorophenoxy)phenyl]acetate in 10 ml of benzene. After 20 minutes, a white solid separates. The mixture is refluxed overnight, cooled and filtered to remove the white solid. The solid is heated in 50 ml of hot chloroform and filtered to remove a small amount of insoluble residue. The filtrate is diluted with 50 ml of hexane and filtered to give the product as white crystals, mp 148.4°–150.5° C.

EXAMPLE 85

Methyl α-(p-tert-butylphenoxy)-α-[p-(p-aminophenoxy)phenyl]acetate

To a suspension of 2.18 g of methyl α-(p-tert-butylphenoxy)-α-[p-(p-nitrophenoxy)phenyl]acetate in 50 ml of methanol was added 160 mg of 10% palladium on carbon and the mixture hydrogenated with shaking. The mixture was filtered and the filtrate concentrated under vacuum to give 2.1 g of the product as a gum.

EXAMPLE 86

Methyl α-(p-tert-butylphenoxy)-α-[p-(p-nitrophenoxy)phenyl]acetate

To a solution of 3.75 g of 4-t-butylphenol in 40 ml of tetrahydrofuran was added 0.88 g of sodium hydride (oil dispersion). After stirring 30 minutes, 1 ml of hexamethylphosphoramide was added and a solution of 7.36 g of methyl α-bromo-α-[p-(p-nitrophenoxy)phenyl]acetate in 25 ml of tetrahydrofuran was added over a period of 30 minutes. The mixture was stirred at room temperature for 30 minutes and refluxed for 30 minutes. The mixture was poured into 130 ml of ice-water and extracted with dichloromethane. The extracts were washed with saturated sodium chloride solution and chilled. Filtration gave 2.1 g of product. The filtrate was concentrated to an oil under vacuum and chromatographed over silica gel (eluent-CCl₄). From the first fractions there was obtained 4.3 g of solid which was dissolved in hot methanol and the volume reduced. Chilling gave 3.7 g of product as pale yellow crystals, mp 101°–103° C.

EXAMPLE 87

Methyl α-bromo-α-[p-(p-nitrophenoxy)phenyl]acetate

A solution of 10.9 g of α-[p-(p-nitrophenoxy)phenyl]acetic acid in 30 ml of thionyl chloride was refluxed 1 hour. The mixture was concentrated under vacuum, benzene was added (twice) and the solvent removed under vacuum to give an oil. The oil was dissolved in 200 ml of carbon tetrachloride and 8.2 g of N-bromosuccinimide added. The mixture was refluxed for 96 hours and 16 ml of methanol added. After refluxing for 1 hour, the solvent was removed under vacuum. Chromatography of the residue over silica gel gave 8.4 g of product as a gum.

EXAMPLE 88

Methyl α-(p-fluorophenoxy)-α-[p-(p-methylsulfonylphenoxy)phenyl]acetate

To a solution of 2.7 g of p-fluorophenol in 20 ml of methanol was added 1.89 g of sodium methoxide. To the solution was added 7.98 g of methyl α-bromo-α-[p-(p-methylsulfonylphenoxy)phenyl]acetate in 40 ml of methanol. The mixture was refluxed and stirred for 18 hours, chilled and filtered to give 4.3 g of white crystals, mp 135°–137° C. Recrystallization from acetone-hexane gave the product as white crystals, mp 136°–138° C.

EXAMPLE 89

Methyl α-(4-chloro-5,6,7,8-tetrahydro-1-naphthyloxy)-α-[p-(p-chlorophenoxy)phenyl]acetate To a solution of 1.19 g of sodium methoxide, 4.57 g of 4-chloro-5,6,7,8-tetrahydro-1-naphthol, and 100 mg of potassium iodide was added 7.11 g of methyl α-bromo-α-[p-(p-chlorophenoxy)phenyl]acetate in 10 ml of benzene. The mixture was heated at reflux overnight, cooled to room temperature, and poured into 100 ml of water. The mixture was then extracted with 2×75 ml of ether. The combined extracts were washed with 2×50 ml of 5% NaOH, 2×50 ml of water, 50 ml of saturated brine, and dried (MgSO₄). Evaporation of the solvent yielded an oil which was chromatographed over 100 g of silica gel (benzene). Concentration of cuts yielded a yellow gum which solidified on standing to give the product as a white solid, mp 87.5°–90° C. (6.4 g).

EXAMPLE 90

Methyl α-(7-chloro-4-indanyloxy)-α-[p-(p-chlorophenoxy)phenyl]acetate

To a solution of 1.19 g of sodium methoxide, 4.22 g of 7-chloro-4-indanol, and 100 mg of potassium iodide in 40 ml of methanol was added 7.11 g of methyl α-bromo-α-[p-(p-chlorophenoxy)phenyl]acetate in 10 ml of benzene. The mixture was heated at reflux overnight, cooled, and then poured into 100 ml of water. The mixture was extracted with 2×75 ml of ether. The combined extracts were washed with 2×50 ml of 5% NaOH, 2×50 ml water, 50 ml saturated brine, and dried (MgSO₄). Evaporation of the solvent yielded a yellow oil which solidified on trituration with petroleum ether to yield 7.14 g of product as a cream colored solid, mp 94°–96° C. The solid was taken up in 75 ml of hot hexane, decanted away from a small amount of oil, and the supernatant liquid cooled to yield 5 g of a cream colored crystal, mp 97°–98.5° C.

EXAMPLE 91

Methyl α-(p-tert-butylphenoxy)-α-[p-(4-chloro-1-naphthyloxy)phenyl]acetate

To a solution of 1.19 g of sodium methoxide, 3.76 g of p-tert-butylphenol, and 50 mg of potassium iodide in 40 ml of methanol was added 8.12 g of methyl α-bromo-α-[p-(4-chloro-1-naphyloxy)phenyl]acetate in 10 ml of benzene. The mixture was heated at reflux overnight, cooled to room temperature, and poured into 100 ml of water. The mixture was then extracted with 2×75 ml of ether. The combined extracts were washed with 2×50 ml of 5% NaOH, 2×50 ml of water, 50 ml of saturated brine and dried (MgSO₄). Evaporation of the solvent gave an amber oil which was chromatographed over 100 g of silica gel (benzene) to give 6.60 g of an amber glass.

EXAMPLE 92

Methyl α-(p-chlorophenoxy)-α-[p-(4-chloro-1-naphthyloxy)-phenyl]acetate

To a solution of 1.19 g of sodium methoxide, 3.21 g of p-chlorophenol and 50 mg of potassium iodide in 40 ml of methanol was added 8.12 g of methyl α-bromo-α-[p-(4-chloro-1-naphthyloxy)phenyl]acetate in 10 ml of benzene. The mixture was refluxed overnight, cooled to room temperature, and then poured into 100 ml of water. The mixture was extracted with 2×75 ml of ether. The combined extracts were washed with 2×50 ml of 5% NaOH, 2×50 ml of water, 50 ml saturated brine, and dried (MgSO$_4$). Evaporation of the solvent yielded an amber oil which was subjected to chromatography on 100 g silica gel (benzene) to afford 6.7 g of an amber glass.

EXAMPLE 93

Methyl p-(4-chloro-1-naphthyloxy)phenylacetate

A solution of 24 g of p-(4-chloro-1-naphthyloxy)acetophenone in 250 ml of methanol containing 42 ml of 70% perchloric acid and 39.5 g of thallium nitrate trihydrate was stirred at 0° C. overnight after which an additional 250 ml of methanol was added, and the stirring was continued for 3 hours at room temperature. The brown solution was then filtered into 1000 ml of water. The mixture was then extracted with 3×150 ml of chloroform. The combined extracts were washed with 2×150 ml of water, 150 ml saturated NaHCO$_3$, 150 ml saturated NaCl and dried (MgSO$_4$). Evaporation of the solvent yielded an orange liquid which was filtered through 100 g of neutral alumina with benzene and concentrated to give 21.85 g of a homogeneous orange liquid. An analytical sample was prepared by bulb-to-bulb distillation (196° C. at 0.1 mm) to give a light yellow liquid.

EXAMPLE 94

Methyl α-(p-cyclohexylphenoxy)-α-[p-(p-tert-butylphenoxy)-phenyl]acetate

In a manner similar to Example 16, 7.54 g of methyl α-bromo-α-[p-(p-tert-butylphenoxy)phenyl]acetate was treated with 4.4 g of p-cyclohexylphenol to give 7.44 g of product as a pale yellow glass.

EXAMPLE 95

Methyl α-(m-tert-butylphenoxy)-α-[p-(p-tert-butylphenoxy)-phenyl]acetate

In a manner similar to Example 16, 7.54 g of methyl α-bromo-α-[p-(p-tert-butylphenoxy)phenyl]acetate was treated with 3.75 g of m-tert-butylphenol to yield 7.4 g of product as a pale yellow glass.

EXAMPLE 96

Methyl α-(α,αα-trifluoro-m-tolyloxy)-α-[p-(p-tert-butylphenoxy)phenyl]acetate

In a manner similar to Example 16, 7.54 g of methyl α-bromo-α-[p-(p-tert-butylphenoxy)phenyl]acetate was treated with 4.05 g of m-trifluoromethylphenol to give 8.07 g of product as a pale yellow glass.

EXAMPLE 97

Methyl α-(p-chlorophenoxy)-α-[p-(p-tert-butylphenoxy)phenyl]acetate

To a solution of 3.21 g of p-chlorophenol, 1.19 g of sodium methoxide and 50 mg of potassium iodide was added 7.54 g of methyl α-bromo-α-[p-(p-tert-butylphenoxy)phenyl]acetate in 10 ml of benzene. The mixture was refluxed overnight and cooled to room temperature. The mixture was then poured into 100 ml of water and extracted with 2×75 ml of ether. The combined extracts were washed with 50 ml of 5% NaOH, 2×50 ml of water, 50 ml saturated brine and dried (MgSO$_4$). Evaporation of the solvent yielded an amber oil. Chromatography on 100 g of silica gel (benzene) afforded 7.36 g of product as a pale yellow glass.

EXAMPLE 98

Methyl α-(p-chlorophenoxy)-α-[p-(α,α,α-trifluoro-m-tolyloxy)phenyl]acetate

In a manner similar to Example 16, 7.62 g of methyl α-bromo-α-[p-(α,α,α-trifluoro-m-tolyloxy)phenyl]acetate was reacted with 3.21 g of p-chlorophenol to give a gel which crystallized on trituration with 50 ml of petroleum ether (6.45 g). Recrystallization from 50 ml of hexane yielded a 5.8 g of a white solid, mp 79°–82° C.

EXAMPLE 99

Methyl α-(p-tert-butylphenoxy)-α-[p-(α,αα-trifluoro-m-tolyloxy)phenyl]acetate

In a manner similar to Example 16, 7.62 g of methyl α-bromo-α-[p-(α,α,α-trifluoro-m-tolyloxy)-phenyl]acetate was reacted with 3.75 g of p-tert-butylphenol to give 6.6 g of product as an amber oil.

EXAMPLE 100

Methyl α-(p-cyclohexylphenoxy)-α-[p-(α,α,α-trifluoro-m-tolyloxy)phenyl]acetate

In a manner similar to Example 16, 7.62 g of methyl α-bromo-α-[p-(α,α,α-trifluoro-m-tolyloxy)phenyl]acetate was reacted with 4.4 g of p-cyclohexylphenol to give 6.5 g of product as an amber oil.

EXAMPLE 101

Methyl α-(p-fluorophenyoxy)-α-[p-(α,α,α-trifluoro-m-tolyloxy)phenyl]acetate

To a solution of 2.8 g of p-fluorophenol, 1.19 g of sodium methoxide, and 50 mg of potassium iodide in 40 ml of methanol was added 7.62 g of methyl α-bromo-α-[p-(α,α,α-trifluoro-m-tolyloxy)phenyl]acetate in 10 ml of benzene. The mixture was refluxed overnight and cooled to room temperature. The mixture was poured into 100 ml of water and extracted with 2×75 ml of ether. The combined extracts were washed with 50 ml of 5% NaOH, 2×50 ml of water, 50 ml of saturated brine and dried (MgSO$_4$). Evaporation of the solvent at reduced pressure yielded an amber oil which was chromatographed on 100 g of silica gel (benzene) to yield 6.7 g of an amber oil which solidified on trituration with petroleum ether, mp 70°–72.5° C.

EXAMPLE 102

Methyl α-(p-chlorophenoxy)-α-[p-(p-chlorophenylthio)phenyl]acetate

In a manner similar to Example 16, 7.43 g of methyl α-bromo-α-[p-(p-chlorophenylthio)phenyl]acetate was reacted with 3.21 g of p-chlorophenol. Ether workup, chromatography and recrystallization from 150 ml of hexane:chloroform (15:1) yielded 5.2 g of a white solid, mp 90.5°–94.5° C.

EXAMPLE 103

Methyl α-(p-tert-butylphenoxy)-α-[p-(p-chlorophenylthio)phenyl]acetate

In a manner similar to Example 16, 7.43 g of methyl α-bromo-α-[p-(p-chlorophenylthio)phenyl]acetate was reacted with 3.75 g of p-tert-butylphenol. Filtration of the crude reaction mixture yielded 5.4 g of white platelets, which yielded 4.8 g of white crystals, mp 106.5°–108.5° C. on recrystallization from 100 ml of 80:20 hexane:chloroform.

EXAMPLE 104

Methyl α-(p-chlorohexylphenoxy)-α-[p-(p-chlorophenylthio)phenyl]acetate

In a manner similar to Example 16, 7.43 g of methyl α-bromo-α-[p-(p-chlorophenylthio)phenyl]acetate was reacted with 4.4 g of 4-cyclohexylphenol. Filtration of the crude reaction mixture yielded 7.12 g of white platelets which yielded 5.5 g of white crystals, mp 122.5°–124.5° C. on recrystallization from 100 ml of methanol-chloroform (4:1).

EXAMPLE 105

Methyl α-(p-fluorophenoxy)-α-[p-(p-chlorophenylthio)phenyl]acetate

To a solution of 2.8 g of p-fluorophenol, 1.19 g of sodium methoxide and 50 mg of potassium iodide in 40 ml of methanol was added 7.43 g of methyl α-bromo-α-[p-(p-chlorophenylthio)phenyl]acetate in 10 ml of benzene. The mixture was refluxed overnight and then cooled to room temperature. The mixture was poured into 100 ml of water and extracted with 2×75 ml of ether. The combined extracts were washed with 50 ml of 5% NaOH, 50 ml water, saturated brine, and dried (MgSO₄). Evaporation of the solvent at reduced pressure afforded an amber oil, which was chromatographed on 100 g of silica gel (benzene). Concentration of the eluate yielded an amber oil which crystallized on trituration with 100 ml of petroleum ether, mp 84.5°–86.5° C. (weight 6.05 g). Recrystallization from 50 ml of hexane yielded 5.3 g of a white solid, mp 84.5°–87° C.

EXAMPLE 106

Copper (II) (p-chlorophenoxy)[p-(p-chlorophenoxy)phenyl]acetate

To a solution of 4.11 g of sodium (p-chlorophenoxy)[p-(p-chlorophenoxy)phenyl]acetate is added 1.25 g of CuSO₄.5H₂O. A pale green solid, formed which is filtered, and washed with water, ethanol, and then ether to give 4.0 g of product.

EXAMPLE 107

Sodium (p-chlorophenoxy)[p-(p-chlorophenoxy)phenyl]acetate

To a solution of 250 g of absolute ethanol in 3 l of benzene is added 1.5 g of sodium. When solution is complete, the solution is refluxed over 454 g of 3A molecular sieves for 36 hours. To the solution is added 146 g of methyl (p-chlorophenoxy)[p-(p-chlorophenoxy)phenyl]acetate. The old sieves are replenished, and the mixture is refluxed for two days, during which time a white solid separated. The sieves are again changed, and refluxing is maintained for another day. The solid is removed by filtration to give 21.5 g of product which is characterized by dissolving in water and acidifying to give the acid, mp 140°–142° C.

EXAMPLE 108

Ethyl (p-chlorophenoxy)[p-(p-chlorophenoxy)phenyl]acetate

To a solution of 250 g of absolute ethanol in 3 l of benzene is added 1.5 g of sodium. When solution is complete, the solution is refluxed over 454 g of 3A molecular sieves for 36 hours. To the solution is added 146 g of methyl (p-chlorophenoxy)[p-(p-chlorophenoxy)phenyl]acetate. The old sieves are replenished, and the mixture is refluxed for two days, during which time a white solid separated. The sieves are again changed, and refluxing is maintained for another day. The solid is removed by filtration to give 21.5 g of white crystals.

The filtrate is concentrated to a brown oil which is filtered through 400 g of silica gel with benzene eluent to give a colorless oil. Trituration with cold hexane gives 112.5 g of white crystals, mp 52.5°–54° C.

EXAMPLE 109

Methyl 2-(p-chlorophenoxy)-2-[p-(p-chlorophenylthio)phenyl]propionate

As described in example 55, a solution of lithium N,N-diisopropylamide in tetrahydrofuran is prepared and chilled to −65° C. to −75° C. To the solution is added dropwise 0.015 mole of methyl (p-chlorophenoxy)[p-(p-chlorophenylthio)phenyl]acetate in 10 ml tetrahydrofuran over 15 minutes. To the mixture is added 4 g of hexamethylphosphoramide and while chilling to −65° C. to −75° C., 4.26 g of methyl iodide is added. After 1 hr., the mixture is allowed to warm to room temperature and stand overnight. The mixture is poured into water and extracted with ether. The extracts are washed with 10% hydrochloric acid, water, saturated NaHCo₃, saturated NaCl solution and dried (MgSO₄). Removal of the solvent under reduced pressure gives the product as an oil.

EXAMPLE 110

Methyl 2-(p-chlorophenoxy)-2-[p-(p-chlorophenylsulfinyl)phenyl]propionate

As described in example 55, a solution of lithium N,N-diisopropylamide in tetrahydrofuran is prepared and chilled to −65° C. to −75° C. To the solution is added 0.015 mole of methyl (p-chlorophenoxy)[p-(p-chlorophenylsulfinyl)phenyl]acetate in 10 ml of tetrahydrofuran. To the mixture is added 5 ml of hexamethylphosphoramide and while chilling to −65° C. to −75° C., 4.26 g of methyl iodide is added. After 1 hr., the mixture is allowed to warm to room temperature and stirr overnight. The mixture is poured into water and extracted with ether. The ether extracts are washed with 10% hydrochloric acid, water, saturated NaHCo3, saturated NaCl solution and dried (MgSO4). Evaporation of the solvent under reduced pressure gives the product as an oil.

EXAMPLE 111

Methyl 2-(p-chlorophenoxy)-2-[p-(p-chlorophenoxy)phenyl]-butyrate

A solution of 0.015 mole of lithium N,N-diisopropylamide (prepared as in example 55) in tetrahydrofuran is chilled to −65° C. to −75° C. To the solution is added methyl (p-chlorophenoxy)[p-(p-chlorophenoxy)phenyl]acetate in 10 ml of tetrahydrofuran. To the mixture is added 5 ml of hexamethylphosphoramide and while chilling to −65° C. to −75° C., 4.68 g of ethyl iodide is added. After 1 hr., the mixture is allowed to warm to room temperature and stirr overnight. The mixture is poured into water and extracted with ether. The ether extracts are washed with 10% hydrochloric acid, water, saturated NaHCo3, saturated NaCl solution and dried (MgSO4). Evaporation of the solvent gives the product as an oil.

EXAMPLE 112

Methyl 2-(4-chloro-3-methylphenoxy)-2-[p-(p-chlorophenoxy)-phenyl]propionate

A solution of 0.015 mole of lithium N,N-diisopropylamide (prepared as in example 55) in tetrahydrofuran is chilled to −65° C. to −75° C. To the solution is added methyl (4-chloro-3-methylphenoxy)[p-(p-chlorophenoxy)phenyl]acetate in tetrahydrofuran. To the mixture is added 5 ml of hexamethylphosphoramide and while chilling to −65° C. to −75° C., 4.26 g of methyl iodide is added. After 1 hr., the mixture is allowed to warm to room temperature and stirr overnight. The mixture is poured into water and extracted with ether. The ether extracts are washed with 10% hydrochloric acid, water, saturated NaHCo3, saturated NaCl solution and dried (MgSO4). Evaporation of the solvent under reduced pressure gives the product as an oil.

EXAMPLE 113

Methyl 2-(5-indanyloxy)-2-[p-(p-chlorophenoxy)phenyl]butyrate

A solution of 0.015 mole of lithium N,N-diisopropylamide (prepared as in example 55) in tetrahydrofuran is chilled to −65° C. to −75° C. To the solution is added methyl (5-indanyloxy)[p-(p-chlorophenoxy)phenyl]acetate in tetrahydrofuran. To the mixture is added 4 ml of hexamethylphosphoramide and while chilling to −65° C. to −75° C., 4.68 g of ethyl iodide is added. After 2 hr., the mixture is allowed to warm to room temperature and stirr overnight. The mixture is poured into water and extracted with ether. The ether extracts are washed with 10% hydrochloric acid, water, saturated NaHCo3, saturated NaCl solution and dried (MgSO4). Evaporation of the solvent gives the product as an oil.

EXAMPLE 114

Methyl[p-(1-methylcyclohexyl)phenoxy][p-(p-chlorophenoxy)phenyl]acetate

In a manner similar to Example 16, 7.11 g of methyl α-bromo-α-[p-(p-chlorophenoxy)phenyl]acetate is reacted with 4.75 g of p-(1-methylcyclohexyl)phenol for 4 hrs. Chilling and filtering gives 7.4 g of product, mp 110°–112° C. Recrystallization from methanol-chloroform gives 6.3 g of white crystals, mp 111°–112.5° C.

EXAMPLE 115

Methyl α-(p-tert-butylphenoxy)α-[p-(p-cyanophenoxy)phenyl]acetate

In a manner similar to Example 66, 4.9 g of methyl α-bromo-α-[p-(p-cyanophenoxy)phenyl]acetate is reacted with 3.6 g p-tert-butylphenol to give 5.7 g of a gum. The gum is passed through column of silica gel with dichloromethanepetroleum ether (bp 30°-60° C.) (75:25) as solvent. The first cuts give a gum which is crystallized from petroleum ether (bp 30°-60° C.)—ether to give 3.2 g of crystals, mp 106°–108° C. Recrystallization from acetone-hexane gives 2.45 g of product as white crystals, mp 122°–124° C.

We claim:

1. A compound of the formula:

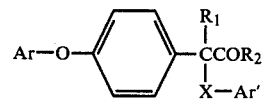

wherein

X is selected from the group consisting of oxygen and sulfur;

R1 is selected from the group consisting of hydrogen and lower alkyl;

R2 is selected from the group consisting of hydroxy, lower alkoxy, lower alkoxyethoxy, 2,3-dihydroxypropoxy and 3-loweralkoxy-2-hydroxypropoxy;

Ar is an aryl selected from the group consisting of 4-chloro-1-naphthyl and substituted phenyl wherein the substituents are cyano, halogen, trifluoromethyl and lower alkyl;

Ar' is an aryl selected from the group consisting of phenyl, 5,6,7,8-tetrahydro-2-naphthyl, 4-chloro-5,6,7,8-tetrahydro-1-naphthyl, 4-indanyl, 5-indanyl, substituted phenyl wherein the phenyl substituents are mono or di-halogen, lower alkyl ($C_1$–$C_3$), mono-t-butyl and cycloalkyl; and where $R_2$ is OH, the alkali metal or organic base carboxylic salts thereof; provided that when Ar is para-t-butylphenyl, Ar' may not be meta-t-butylphenyl; and further provided that when Ar is α,α,α-trifluoro-meta-toyl, Ar' may not be para-fluorophenyl.

2. A compound of the formula:

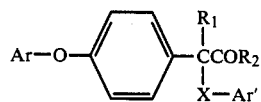

wherein

X is selected from the group consisting of oxygen and sulfur;

R₁ is selected from the group consisting of hydrogen and lower alkyl;

R₂ is selected from the group consisting of hydroxy, lower alkoxy, lower alkoxyethoxy, 2,3-dihydroxypropoxy and 3-loweralkoxy-2-hydroxypropoxy;

Ar is an aryl selected from the group consisting of 4-chloro-1-naphthyl and substituted phenyl wherein the substituents are cyano, halogen, trifluoromethyl and lower alkyl;

Ar' is an aryl selected from the group consisting of phenyl, 5,6,7,8-tetrahydro-1-naphthyl, 5,6,7,8-tetrahydro-2-naphthyl, 4-chloro-5,6,7,8-tetrahydro-1-naphthyl, 4-indanyl, 5-indanyl, and substituted phenyl wherein the substituents are mono or dihalogen, lower alkyl ($C_1$–$C_3$), mono-t-butyl, cyclohexyl, cyclopentyl and adamantyl;

And where R₂ is OH, the alkali metal or organic base carboxylic salts thereof; provided that when Ar is para-t-butylphenyl, Ar' may not be meta-t-butylphenyl; and further provided that when Ar is α,α,α-trifluoro-meta-tolyl, Ar' may not be para-fluorophenyl.

3. A compound of the formula:

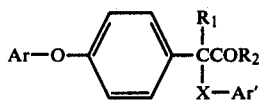

wherein

X is selected from the group consisting of oxygen and sulfur;

R₁ is selected from the group consisting of hydrogen and lower alkyl;

R₂ is selected from the group consisting of hydroxy lower alkoxy, lower alkoxyethoxy, 2,3-dihydroxypropoxy and 3-loweralkoxy-2-hydroxypropoxy;

Ar is an aryl selected from the group consisting of 4-chloro-1-naphthyl and mono or di-substituted phenyl wherein the substituents are cyano, chloro, fluoro, trifluoromethyl and lower alkyl;

Ar' is an aryl selected from the group consisting of phenyl, 5,6,7,8-tetrahydro-1-naphthyl, 5,6,7,8-tetrahydro-2-naphthyl, 4-chloro-5,6,7,8-tetrahydro-1-naphthyl, 4-indanyl, 5-indanyl, and mono or di-substituted phenyl wherein the phenyl substituents are chloro, fluoro, lower alkyl ($C_1$–$C_3$), mono-t-butyl, cyclohexyl, cyclopentyl and adamantyl;

And where R₂ is OH, the alkali metal or organic base carboxylic salts thereof; provided that when Ar is para-t-butylphenyl, Ar' may not be meta-t-butylphenyl; and further provided that when Ar is α,α,α-trifluoro-meta-tolyl, Ar' may not be para-fluorophenyl.

4. The compound according to claim 1 wherein Ar and Ar' are p-chlorophenyl, X is oxygen, R₁ is hydrogen, R₂ is ethoxy: Ethyl α-(p-chlorophenoxy)-α-[p-(p-chlorophenoxy)phenyl]acetate.

5. The compound according to claim 1 wherein Ar is p-chlorophenyl, X is oxygen, R₁ is hydrogen, R₂ is ethoxy and Ar' is p-fluorophenyl: Ethyl α-(p-fluorophenoxy)-α-[p-(p-chlorophenoxy)phenyl]acetate.

6. The compound according to claim 1 wherein Ar is p-chlorophenyl, X is oxygen, R₁ is hydrogen, R₂ is ethoxy and Ar' is p-tert-butyl phenyl: Ethyl α-(p-tert-butyl phenoxy)-α-[p-(p-chlorophenoxy)phenyl]acetate.

7. The compound according to claim 1 wherein Ar is p-chlorophenyl, X is oxygen, R₁ is methyl, R₂ is ethoxy and Ar' is 4-chloro-3-methylphenyl: Ethyl 2-(4-chloro-3-methylphenoxy)-2-[p-(p-chlorophenoxy)phenyl]propionate.

8. The compound according to claim 1 wherein Ar is p-chlorophenyl, X is oxygen, R₁ is hydrogen, R₂ is ethoxy and Ar' is 4-chloro-3-methylphenyl: Ethyl α-(4-chloro-3-methylphenoxy)-α-[p-(p-chlorophenoxy)phenyl]acetate.

9. The compound according to claim 1 wherein Ar is p-chlorophenyl, X is oxygen, R₁ is hydrogen, R₂ is ethoxy and Ar' is m-tert-butyl phenyl: Ethyl α-(m-tert-butylphenoxy)-α-[p-(p-chlorophenoxy)phenyl]acetate.

10. The compound according to claim 1 wherein Ar is p-chlorophenyl, X is oxygen, R₁ is hydrogen, R₂ is ethoxy and Ar' is 5-indanyl: Ethyl α-(5-indanyloxy)-α-[p-(p-chlorophenoxy)phenyl]acetate.

11. The compound according to claim 1 wherein Ar and Ar' are p-chlorophenyl, X is oxygen, R₁ is methyl and R₂ is ethoxy: Ethyl 2-(p-chlorophenoxy-2-[p-(p-chlorophenoxy)phenyl]propionate.

12. The compound wherein Ar is p-chlorophenyl, X is oxygen, R₁ is hydrogen, R₂ is ethoxy and Ar' is p-(1-methylcyclohexyl)phenyl: Ethyl α-[p-(1-methylcyclohexyl)phenoxy]-α-[p-(p-chlorophenoxy)phenyl]acetate.

* * * * *